US010053479B2

(12) United States Patent
Konno et al.

(10) Patent No.: US 10,053,479 B2
(45) Date of Patent: Aug. 21, 2018

(54) RAW MATERIAL AND PRODUCTION METHOD FOR CYCLOMETALATED IRIDIUM COMPLEX

(71) Applicants: TANAKA KIKINZOKU KOGYO K.K., Chiyoda-ku, Tokyo (JP); NATIONAL INSTITUTE OF ADVANCED INDUSTRIAL SCIENCE AND TECHNOLOGY, Chiyoda-ku, Tokyo (JP)

(72) Inventors: Hideo Konno, Tsukuba (JP); Junichi Taniuchi, Tsukuba (JP); Ryosuke Harada, Tsukuba (JP); Toshiyuki Shigetomi, Tsukuba (JP); Yasushi Masahiro, Tokyo (JP)

(73) Assignees: TANAKA KIKINZOKU KOGYO K.K., Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/109,927

(22) PCT Filed: Dec. 16, 2014

(86) PCT No.: PCT/JP2014/083217
§ 371 (c)(1),
(2) Date: Jul. 6, 2016

(87) PCT Pub. No.: WO2015/104961
PCT Pub. Date: Jul. 16, 2015

(65) Prior Publication Data
US 2016/0326198 A1    Nov. 10, 2016

(30) Foreign Application Priority Data
Jan. 10, 2014 (JP) ................ 2014-002943

(51) Int. Cl.
*C07C 49/92* (2006.01)
*C07F 15/00* (2006.01)

(52) U.S. Cl.
CPC .......... *C07F 15/0033* (2013.01); *C07C 49/92* (2013.01); *C07F 15/004* (2013.01)

(58) Field of Classification Search
CPC .................................. C07F 15/0033
USPC ............................................ 546/4
See application file for complete search history.

(56) References Cited

U.S. PATENT DOCUMENTS

| 6,753,437 B1 * | 6/2004 | Sagae | C07C 49/92 |
| | | | 106/1.28 |
| 7,517,984 B2 * | 4/2009 | Huo | C07F 15/0033 |
| | | | 546/4 |
| 7,994,319 B2 * | 8/2011 | Igarashi | C07F 15/0033 |
| | | | 546/10 |
| 8,759,521 B2 * | 6/2014 | Chi | C07F 15/0053 |
| | | | 136/263 |

FOREIGN PATENT DOCUMENTS

| JP | H07-316176 A | 12/1995 |
| JP | H08-085873 A | 4/1996 |
| JP | H11-255700 A | 9/1999 |
| JP | 2000-212744 A | 8/2000 |
| JP | 2000-319236 A | 11/2000 |
| JP | 2001-233880 A | 8/2001 |
| JP | 2002-105055 A | 4/2002 |
| JP | 2002-540572 A | 11/2002 |
| JP | 2003-064019 A | 3/2003 |
| JP | 2003-321415 A | 11/2003 |
| JP | 2003-321416 A | 11/2003 |
| JP | 2004-337802 A | 12/2004 |
| JP | 2005-035902 A | 2/2005 |
| JP | 2005-516040 A | 6/2005 |
| JP | 2006-063080 A | 3/2006 |
| JP | 2006-104201 A | 4/2006 |
| JP | 2006-111623 A | 4/2006 |
| JP | 2006-213723 A | 8/2006 |
| JP | 2006-290891 A | 10/2006 |
| JP | 2006-523231 A | 10/2006 |
| JP | 2007-504272 A | 3/2007 |
| JP | 2007-513158 A | 5/2007 |
| JP | 2007-513159 A | 5/2007 |
| JP | 2007-224025 A | 9/2007 |
| JP | 2008-504342 A | 2/2008 |
| JP | 2008-505076 A | 2/2008 |
| JP | 2008-514005 A | 5/2008 |
| JP | 2009-522228 A | 6/2009 |
| JP | 2009-526071 A | 7/2009 |
| JP | 2009-541431 A | 11/2009 |
| JP | 2009-544167 A | 12/2009 |
| JP | 2012-006914 A | 1/2012 |
| JP | 4913059 B2 | 1/2012 |
| JP | 4917751 B2 | 2/2012 |
| JP | 2013-136567 A | 7/2013 |
| JP | 2013-536170 A | 9/2013 |
| WO | WO 2010/086089 A1 | 8/2010 |

OTHER PUBLICATIONS

Dedeian , Inorg. Chem., vol. 30, p. 1685, 1991.*

(Continued)

*Primary Examiner* — Nizal S Chandrakumar
(74) *Attorney, Agent, or Firm* — Orrick, Herrington & Sutcliffe LLP; Joseph Calvaruso

(57) ABSTRACT

The present invention relates to a raw material for a cyclometalated iridium complex, and provides a technique that makes it possible to obtain a cyclometalated iridium complex in higher yield at a lower reaction temperature than using tris(2,4-pentanedionato)iridium(III). The present invention relates to a raw material for a cyclometalated iridium complex, including an organic iridium material for producing a cyclometalated iridium complex, the organic iridium material being a tris(β-diketonato)iridium(III), in which an asymmetric β-diketone is coordinated to iridium.

6 Claims, No Drawings

(56) References Cited

OTHER PUBLICATIONS

Dedeian, Inorg. Chem. 1991, 30, 1685-1687 1685.*
Dorwald F. A. Side Reactions in Organic Synthesis, 2005, Wiley: VCH, Weinheim p. IX of Preface p. 1-15.*
International Search Report for PCT/JP2014/083217, dated Mar. 24, 2015.
King et al, Excited-State Properties of a Triply Ortho-Metalated Iridium (III) Complex, J.Am. Chem. Soc., 1985, vol. 107, pp. 1431-1432, American Chemical Society.
Zhang et al., a New Synthetic Route to the Preparation of a Series of Strong Photoreducing Agents: fac Tris-Ortho-Metalated Complexes of Iridium (III) with Substituted 2-Phenylpyridines, Inorg. Chem. 1991, vol. 30, No. 8, pp. 1685-1687, American Chemical Society.
Collins et al., Synthesis, Characterization, and Molecular Structure of Bis(tetraphenylcyclopentadienyl)rhodium (II), Organometallics 1995, vol. 14, No. 3, pp. 1232-1238, American Chemical Society.

* cited by examiner

RAW MATERIAL AND PRODUCTION METHOD FOR CYCLOMETALATED IRIDIUM COMPLEX

TECHNICAL FIELD

The present invention relates to a raw material and a production method for a cyclometalated iridium complex, and a technique for providing cyclometalated iridium complexes applicable to organic electroluminescent (EL) devices, organic electrochemiluminescent (ECL) devices, luminescent sensors, photosensitizing pigments, various light sources, and the like.

BACKGROUND ART

"Cyclometalated iridium complex" is a general term for organic iridium complexes, in which multidentate ligands are coordinated to the iridium atom to form a ring, and at least one iridium-carbon bond is present, for example, tris(2-phenylpyridine)iridium [Ir(ppy)$_3$] (Chemical Formula 1). Among cyclometalated iridium complexes coordinated with, as a ligand, an aromatic heterocyclic bidentate ligand such as a 2-phenylpyridine derivative, a 2-phenylquinoline derivative, or a 1-phenylisoquinoline derivative as in Chemical Formula 1 are used as phosphorescent materials for organic electroluminescent (EL) devices, organic electrochemiluminescent (ECL) devices, and the like (Patent Document 1). Phosphorescent materials have light-emitting efficiency about 3 to 4 times higher than that of fluorescent materials conventionally used in the development of organic EL devices, etc., and thus are expected to be put into practical use to achieve higher efficiency/energy saving.

[Chemical Formula 1]

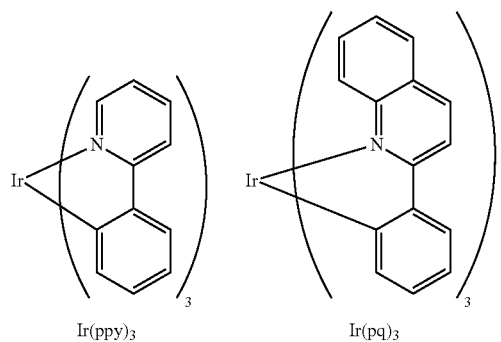

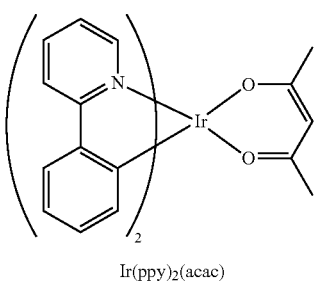

Ir(ppy)$_2$(acac)

Examples of cyclometalated iridium complexes include a biscyclometalated iridium complex, in which two aromatic heterocyclic bidentate ligands are coordinated to the iridium atom, and a triscyclometalated iridium complex, in which three aromatic heterocyclic bidentate ligands are coordinated to the iridium atom. Among them, triscyclometalated iridium complexes have particularly high thermal stability and, when applied to organic EL devices, etc., are expected to increase the life.

Such a cyclometalated iridium complex can be synthesized in a single step, for example, by allowing iridium trichloride as a raw material to react with an aromatic heterocyclic bidentate ligand such as 2-phenylpyridine (ppy) (Chemical Formula 2, Non-Patent Document 1). Additionally, a cyclometalated iridium complex can be obtained in a single step by allowing, as a raw material, tris(2,4-pentanedionato)iridium(III) (hereinafter sometimes referred to as Ir(acac)$_3$), in which three 2,4-pentanediones are coordinated to iridium, to react with an aromatic heterocyclic bidentate ligand such as 2-phenylpyridine (ppy) (Chemical Formula 3, Non-Patent Document 2). Further, Patent Document 2 discloses a method including allowing iridium trichloride as a raw material to react with an aromatic heterocyclic bidentate ligand such as 2-phenylpyridine (ppy) to perform multi-step synthesis method via a chlorine-crosslinked dimer (Chemical Formula 4).

[Chemical Formula 2]

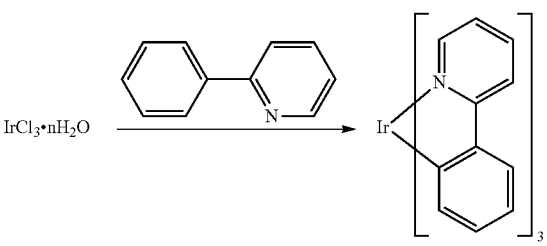

[Chemical Formula 3]

-continued

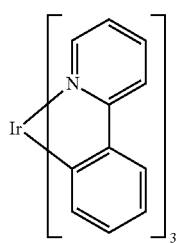

[Chemical Formula 4]

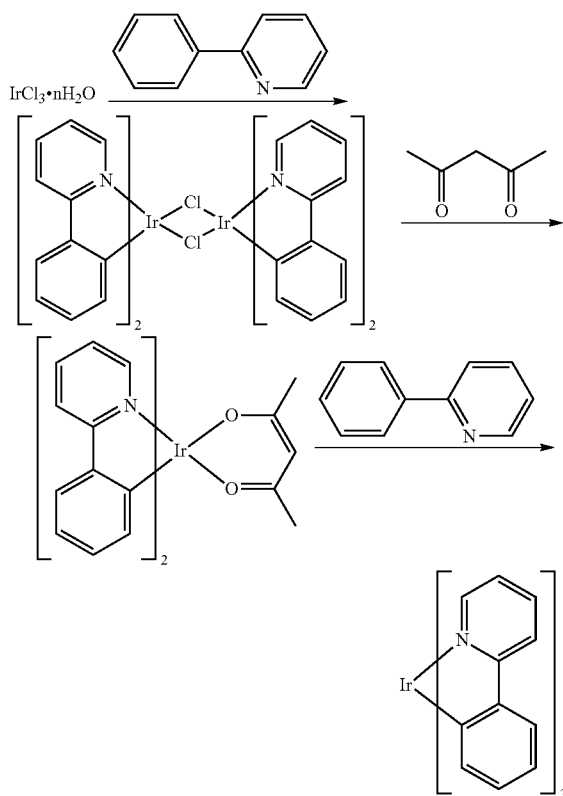

However, a cyclometalated iridium complex obtained by single-step synthesis using iridium trichloride as a raw material as in Non-Patent Document 1 is problematic in that a chlorine component derived from iridium trichloride remains in the cyclometalated iridium complex. It has been pointed out that such a chlorine component adversely affects the light-emitting properties when applied to an organic EL device (Patent Document 3).

Meanwhile, in Non-Patent Document 2, non-chlorine tris(2,4-pentanedionato)iridium(III) is used as a raw material, and thus a chlorine component derived from the iridium raw material does not remain at all. However, tris(2,4-pentanedionato)iridium(III) is thermally stable and has low reactivity, and thus has been problematic in that the synthesis yield of the cyclometalated iridium complex is low.

Specifically, because tris(2,4-pentanedionato)iridium(III) is thermally stable, in order to obtain a cyclometalated iridium complex in good yield, generally, the synthesis is performed under high-temperature conditions at 200° C. or more. Therefore, sometimes, an unexpected decomposition reaction proceeds, and the yield or purity was reduced. Additionally, it has been pointed out that due to 2,4-pentanedione produced with the progress of the reaction, the temperature in the reaction solution becomes less likely to rise sufficiently, causing a decrease in the yield of the cyclometalated iridium complex (Patent Document 4).

Additionally, tris(2,4-pentanedionato)iridium(III) has symmetric R-diketone ligands, and thus has excellent crystallinity and is in a solid state at room temperature. Such tris(2,4-pentanedionato)iridium(III) in a solid state has sublimability. According to the findings of the present inventors, in the course of producing a cyclometalated iridium complex, tris(2,4-pentanedionato)iridium(III) may deposit on the top of the reaction vessel and come out of the reaction system. This is considered to be another cause of a decrease in the yield of the cyclometalated iridium complex.

Therefore, when a cyclometalated iridium complex is obtained using tris(2,4-pentanedionato)iridium(III) as a raw material, in order to improve the yield of the cyclometalated iridium complex, adding a reaction promoter to the reaction system is proposed. Patent Document 5 and Patent Document 3 describes the addition of a Lewis acid and a Bronsted acid, respectively, as a reaction promoter to the reaction system in obtaining a cyclometalated iridium complex.

However, the production methods described in Patent Document 3 and Patent Document 5 have fundamental problems in that they cannot be applied when aromatic heterocyclic bidentate ligands or the reaction product is unstable to acids. Therefore, with these production methods, the yield of the cyclometalated iridium complex cannot be necessarily improved sufficiently, and the development of a novel production method has been craved. Further, the production method disclosed in Patent Document 2 is a multi-step synthesis method, and thus takes time and effort and also requires the isolation/purification of the product in each step. Therefore, there are disadvantages in terms of production cost.

RELATED ART DOCUMENT

Patent Documents

Patent Document 1: JP 2012-6914 A
Patent Document 2: JP 2002-105055 A
Patent Document 3: JP 4913059 B2
Patent Document 4: JP 2004-337802 A
Patent Document 5: JP 4917751 B2

Non-Patent Documents

Non-Patent Document 1: J. Am Chem. Soc., Vol. 107, p. 1431, 1985
Non-Patent Document 2: Inorg. Chem., Vol. 30, p. 1685, 1991

SUMMARY OF THE INVENTION

Problems to be Solved by the Invention

In view of the above background, the present invention relates to a non-chlorine raw material for a cyclometalated iridium complex (hereinafter sometimes referred to as organic iridium material or iridium raw material), and an object of the present invention is to provide a technique that makes it possible to obtain a cyclometalated iridium complex from an iridium raw material by a single-step synthesis reaction in higher yield at a lower reaction temperature than using tris(2,4-pentanedionato)iridium(III).

Means for Solving the Problems

In order to solve the above problems, starting from tris(2,4-pentanedionato)iridium(III), which is a raw material containing no chlorine atom, the present inventors have conducted extensive research to improve the reactivity with an aromatic heterocyclic bidentate ligand. As a result, they have focused attention on an iridium raw material having asymmetric substituents as β-diketone ligands, and thus conceived of the present invention.

The present invention relates to a raw material and a production method for a cyclometalated iridium complex, in which an organic iridium material serves as a raw material for producing a cyclometalated iridium complex, the organic iridium material is a tris(β-diketonato)iridium(III) represented by General Formula (1), in which an asymmetric β-diketone is coordinated to iridium. In General Formula (1), $R^a$ and $R^b$ are each a hydrocarbon group or a heterocyclic group, $R^c$ is a hydrogen atom, a hydrocarbon group, or a heterocyclic group, O is an oxygen atom, and Ir is an iridium atom.

[Chemical Formula 5]

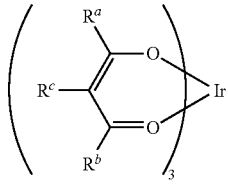

General Formula (1)

The raw material of the present invention is composed of an organic iridium material in which three β-diketones having the same structure are coordinated to iridium, and characterized in that the β-diketone is asymmetric. Specifically, in the above General Formula (1), substituents $R^a$ and $R^b$ in the β-diketone are different kinds of substituents. When the raw material of the present invention is used, a cyclometalated iridium complex can be produced in better yield at a lower reaction temperature as compared with using tris(2,4-pentanedionato)iridium(III), which has been conventionally used as a raw material.

As the substituents $R^a$, $R^b$, and $R^c$ in the β-diketone, the following substituents are possible specifically. The substituents $R^a$ and $R^b$ are hydrocarbon groups or heterocyclic rings, and $R^a$ and $R^b$ are not the same because the structure is asymmetric. $R^c$ is a hydrogen atom, a hydrocarbon group, or a heterocyclic group. $R^a$ and $R^c$, or $R^b$ and $R^c$, may be joined together to form a saturated hydrocarbon ring or an unsaturated hydrocarbon ring.

When $R^a$ and/or $R^b$ is a hydrocarbon group, an aliphatic hydrocarbon group or an aromatic hydrocarbon group is preferable, an aliphatic hydrocarbon group is more preferable, and a linear or branched hydrocarbon group is particularly preferable. Here, aliphatic hydrocarbon in the present invention means hydrocarbons other than aromatic hydrocarbons and includes non-aromatic cyclic hydrocarbons. When $R^a$ and $R^b$ are aliphatic hydrocarbon groups, a cyclometalated iridium complex can be produced in even better yield.

When $R^a$ and/or $R^b$ is an aliphatic hydrocarbon group, a $C_{1-20}$ aliphatic hydrocarbon group is preferable, an alkyl group (preferably $C_{1-10}$, and more preferably $C_{1-5}$, such as a methyl group, an ethyl group, a propyl group, an isopropyl group, an n-butyl group, a t-butyl group, an n-octyl group, an n-decyl group, an n-hexadecyl group, a cyclopropyl group, a cyclopentyl group, a cyclohexyl group, or a neopentyl group), an alkenyl group (preferably $C_{2-10}$, more preferably $C_{2-5}$, such as vinyl, allyl, 2-butenyl, or 3-pentenyl), or an alkynyl group (preferably $C_{2-10}$, more preferably $C_{2-5}$, such as propargyl or 3-pentynyl) is more preferable, an alkyl group is still more preferable, and a methyl group, an ethyl group, a propyl group, an isopropyl group, an n-butyl group, or a t-butyl group is particularly preferable. Either $R^a$ or $R^b$ being a methyl group is particularly preferable. Hydrogen atoms in these aliphatic hydrocarbon groups may be substituted with substituents R and $R^1$ to $R^{48}$ defined below, and fluorine substitution is also preferable.

When $R^a$ and/or $R^b$ is an aromatic hydrocarbon group, a $C_{6-20}$ aromatic hydrocarbon group is preferable, and a $C_{6-10}$ aromatic hydrocarbon group is more preferable. Specific examples of aromatic hydrocarbon groups include a phenyl group, a naphthyl group, a biphenyl group, a fluorenyl group, a phenanthryl group, an anthracenyl group, a triphenylenyl group, a terphenyl group, a pyrenyl group, a mesityl group, a tolyl group, a xylyl group, an azulenyl group, an acenaphthenyl group, and an indenyl group. Hydrogen atoms in these aromatic hydrocarbon groups may be substituted with substituents R and $R^1$ to $R^{48}$ defined below, and fluorine substitution is also preferable.

When $R^a$ and/or $R^b$ is a heterocyclic group, a $C_{1-20}$ heterocyclic group is preferable, and a $C_{1-10}$ heterocyclic group is more preferable. Specific examples of heterocyclic groups include a pyridyl group, a pyrazinyl group, a pyrimidyl group, a pyridazinyl group, a pyrrolyl group, a pyrazolyl group, a triazolyl group, an imidazolyl group, an oxazolyl group, a thiazolyl group, an isoxazolyl group, an isothiazolyl group, a quinolyl group, a furyl group, a thienyl group, a selenophenyl group, a tellurophenyl group, a piperidyl group, a piperidino group, a morpholino group, a pyrrolidyl group, a pyrrolidino group, a benzisoxazolyl group, a benzimidazolyl group, a benzothiazolyl group, a carbazolyl group, an azepinyl group, and a silolyl group. Hydrogen atoms in these heterocyclic groups may be substituted with substituents R and $R^1$ to $R^{48}$ defined below.

When $R^a$ and $R^c$, or $R^b$ and $R^c$, are joined together to form a saturated or unsaturated hydrocarbon ring, preferable modes are as represented by the following General Formula (2).

[Chemical Formula 6]

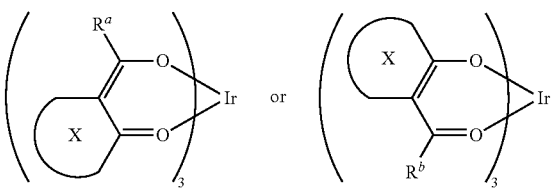

General Formula (2)

(In General Formula (2), Ir represents iridium. O represents an oxygen atom. $R^a$ and $R^b$ each represent a hydrocarbon group or a heterocyclic group. X represents a 5- or 6-membered saturated or unsaturated hydrocarbon ring composed of carbon or hydrogen.)

In General Formula (2), the substituents that $R^a$ and $R^b$ may represent are as defined in General Formula (1), and their suitable ranges are also the same. X represents a 5- or 6-membered saturated or unsaturated hydrocarbon ring, which is preferably $C_{5-20}$, and more preferably $C_{5-10}$.

Examples of asymmetric β-diketones in the present invention are described in JP 8-85873 A, JP 2000-212744 A, JP 2003-64019 A, JP 2003-321416 A, JP 2005-35902 A, JP 2013-136567 A, etc. These asymmetric β-diketone ligands are commercially available, and can also be easily produced by the methods described in, for example, in addition to the above patent documents, JP 11-255700 A, JP 2000-319236 A, JP 2001-233880 A, etc.

$R^c$ in General Formula (1) is preferably a hydrogen atom or a hydrocarbon group, and more preferably a hydrogen atom. Hydrocarbon groups or heterocyclic groups preferable as $R^c$ are the same as the substituents suitable as $R^a$ and $R^b$ described above.

The iridium raw material of the present invention represented by General Formula (1) can be produced with reference to the methods described in JP 7-316176 A, JP 2003-321415 A, JP 2003-321416 A, JP 2003-64019 A, Organometallics, 1995, Vol. 14, No. 3, p. 1232, etc.

Typical examples (A-1) to (A-80) of iridium raw materials represented by General Formula (1) are as follows, but the present invention is not limited thereto.

[Chemical Formula 7]

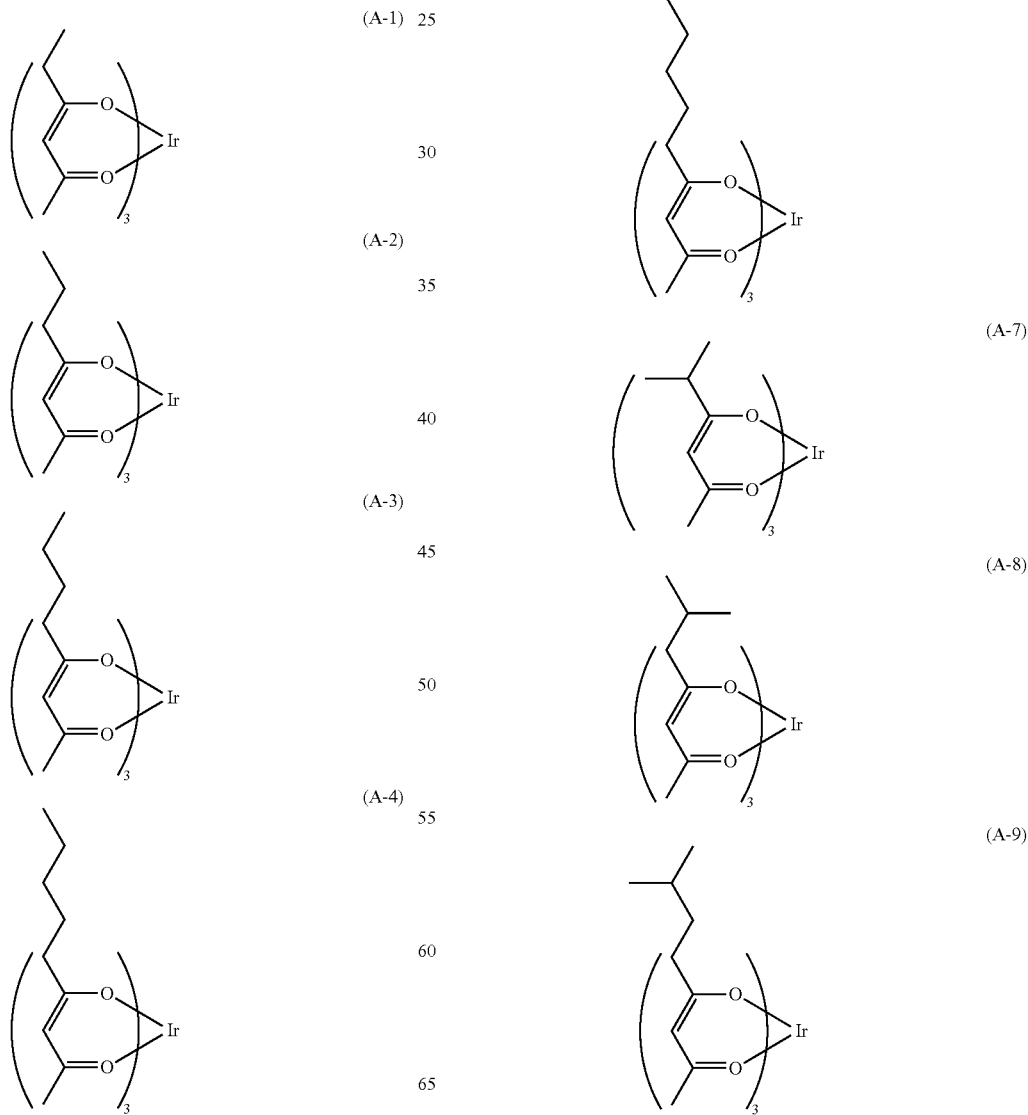

(A-10)
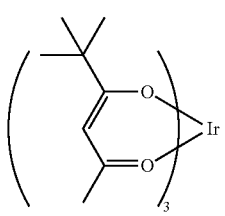
(A-11)
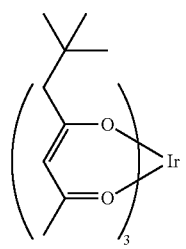
(A-12)
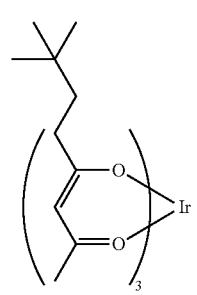
(A-13)
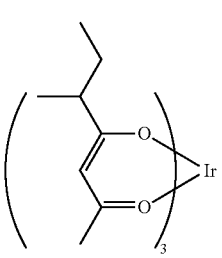
(A-14)
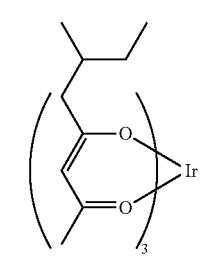
(A-15)
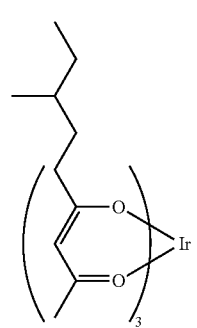
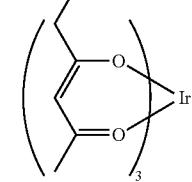
(A-16)
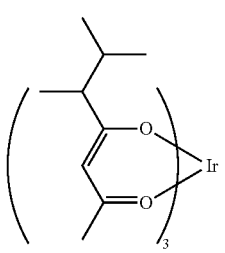
(A-17)
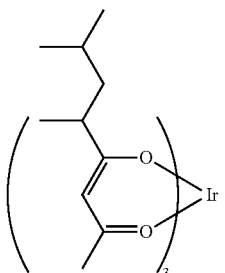
(A-18)
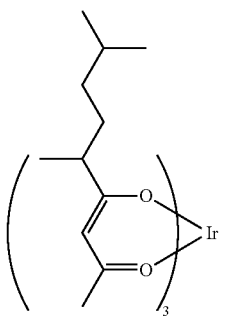
(A-19)
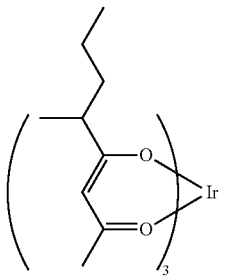
(A-20)
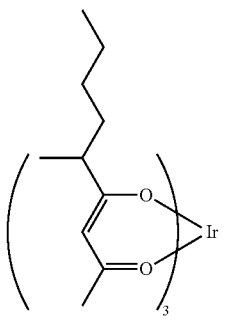

(A-21) 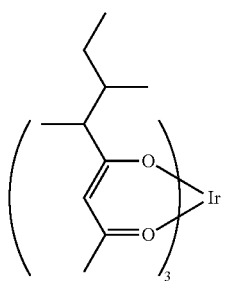
(A-22) 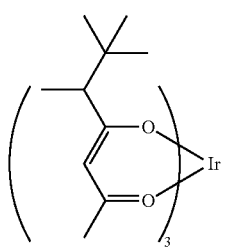
(A-23) 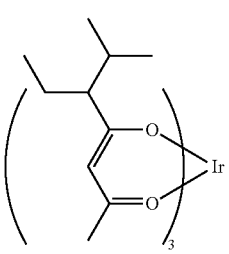
(A-24) 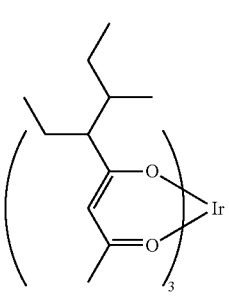
(A-25) 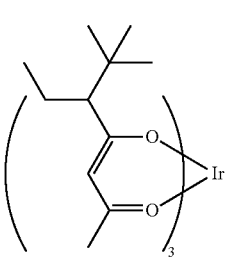
[Chemical Formula 8]
(A-26) 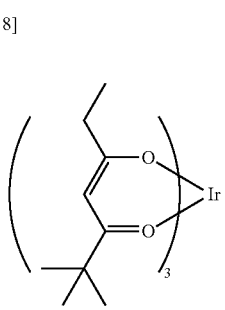
(A-27) 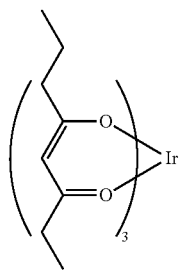
(A-28) 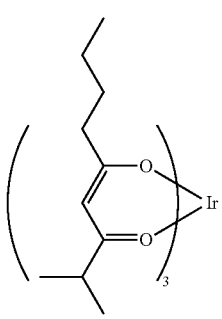
(A-29) 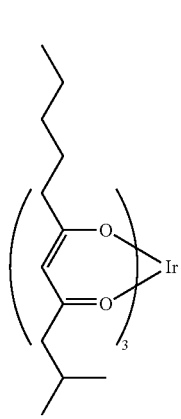
(A-30) 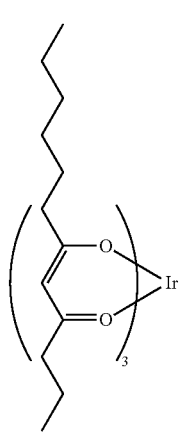

(A-31)
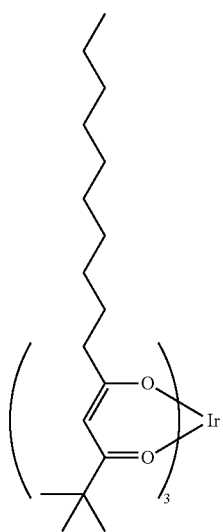
(A-32)
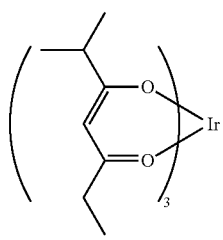
(A-33)
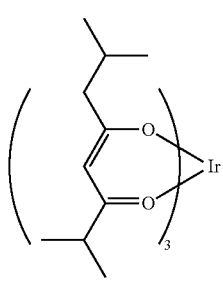
(A-34)
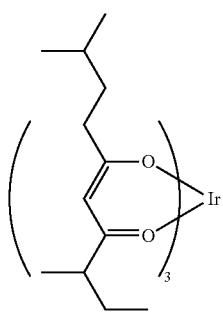
(A-35)
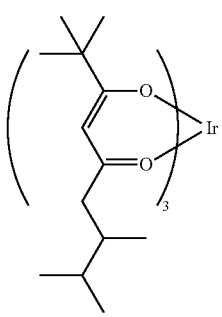
(A-36)
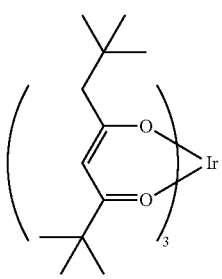
(A-37)
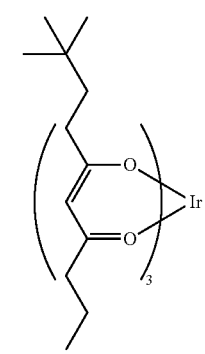
(A-38)
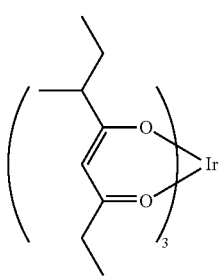
(A-39)
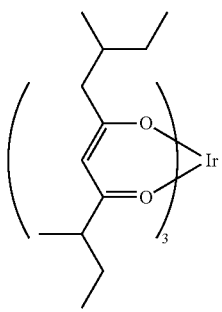

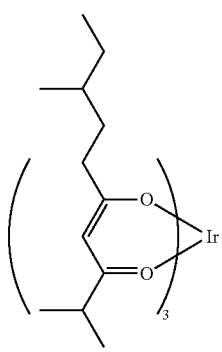 (A-40)
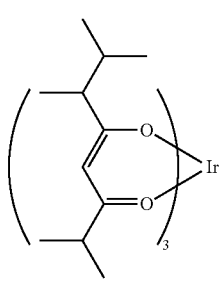 (A-41)
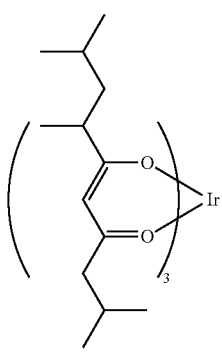 (A-42)
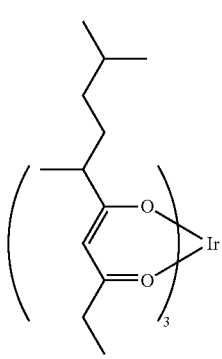 (A-43)
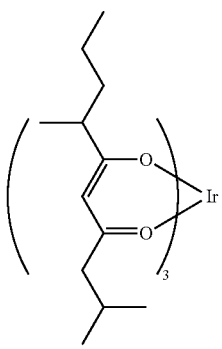 (A-44)
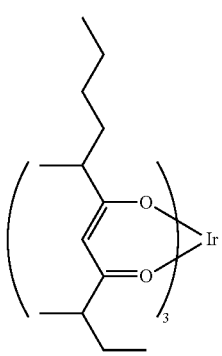 (A-45)
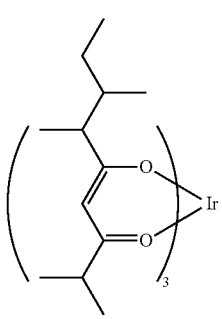 (A-46)
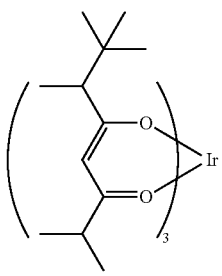 (A-47)
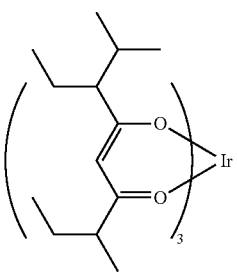 (A-48)

(A-49)
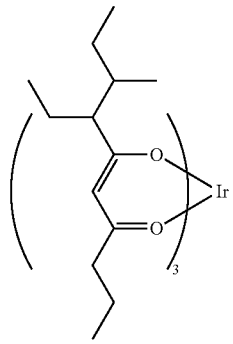
(A-50)
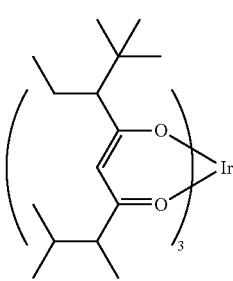
[Chemical Formula 9]
(A-51)
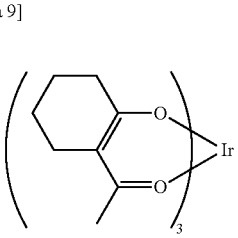
(A-52)
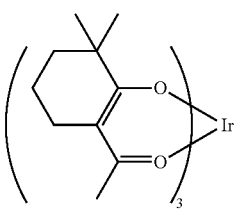
(A-53)
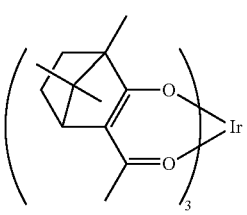
(A-54)
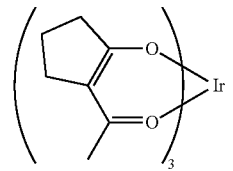
(A-55)
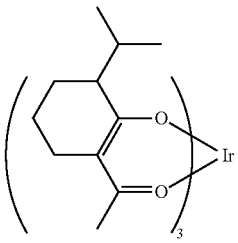
(A-56)
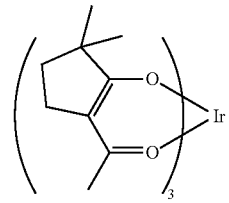
(A-57)
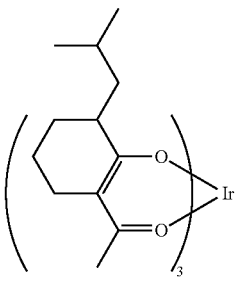
(A-58)
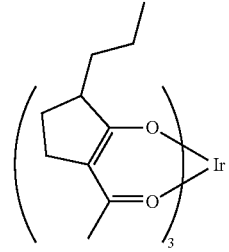
(A-59)
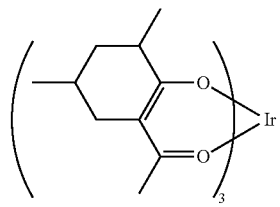
(A-60)
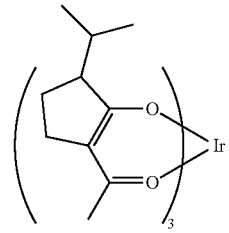
(A-61)
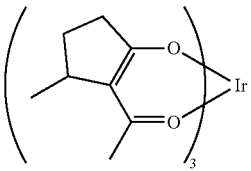

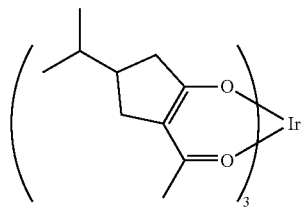 (A-62)
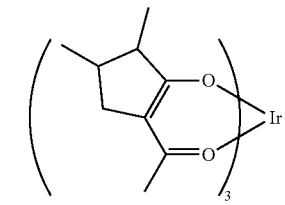 (A-63)
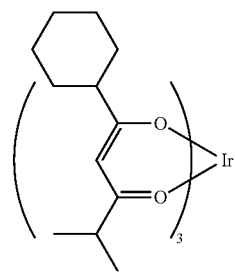 (A-64)
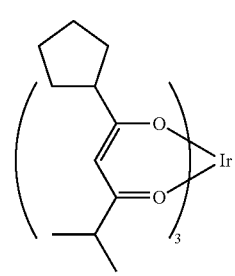 (A-65)
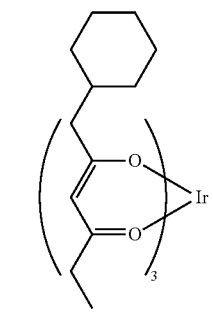 (A-66)
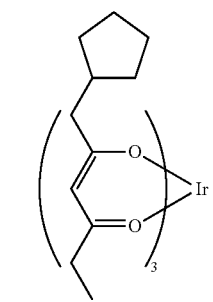 (A-67)
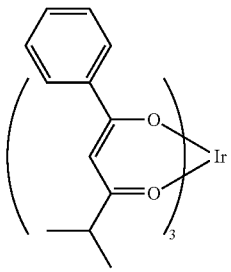 (A-68)
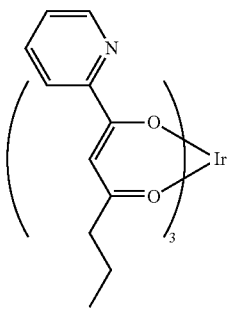 (A-69)
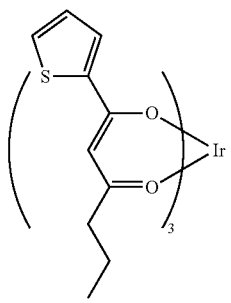 (A-70)
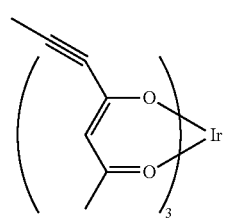 (A-71)
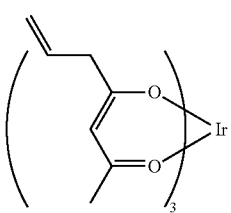 (A-72)

(A-73) 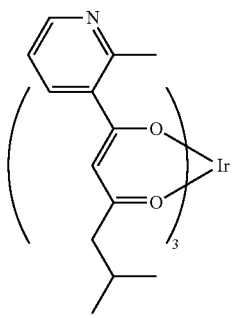

(A-74) 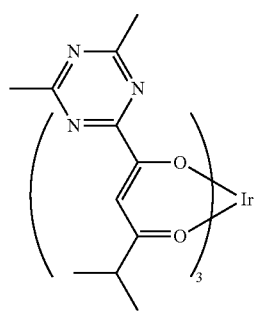

(A-75) 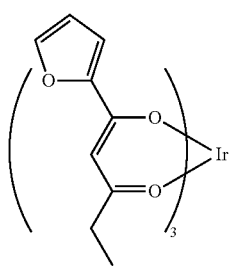

(A-76) 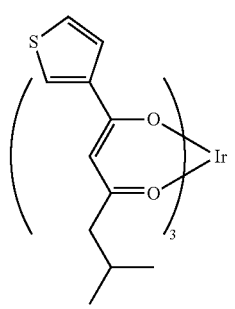

(A-77) 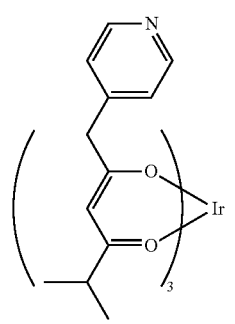

(A-78) 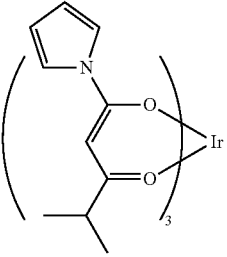

(A-79) 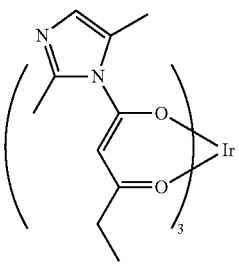

(A-80) 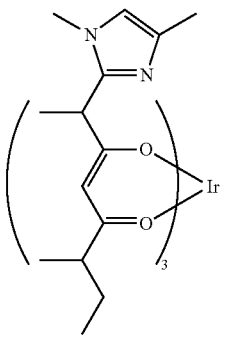

Examples of iridium raw materials represented by General Formula (1) are shown in (A-1) to (A-80). Among them, (A-1) to (A-50) are preferable, (A-1) to (A-25) are more preferable, and (A-3) and (A-7) are particularly preferable.

Additionally, of iridium raw materials represented by General Formula (1), raw materials whose 5% weight loss temperature measured by a TG-DTA simultaneous measuring instrument is lower than the temperature measured from tris(2,4-pentanedionato)iridium(III) are preferable. Incidentally, the 5% weight loss temperature varies depending on the measurement conditions. For example, a raw material whose 5% weight loss temperature at a temperature rise rate of 5° C./min, in a nitrogen gas flow (200 mL/min), and at ambient pressure is less than 222° C. is preferable.

An iridium raw material represented by General Formula (1) has a steric structure in which three β-diketone ligands are in octahedral arrangement around the iridium metal. In this steric structure, because the β-diketone ligands are asymmetric, two kinds of geometric isomers (facial isomer and meridional isomer) are present. A facial isomer and a meridional isomer are named by the nomenclature for isomers of a hexadentate octahedral complex and described in "Yuki-Kinzoku Kagaku-Kiso to Oyo (Organometal Chemistry—Basis and Application)", Akio Yamamoto (Shokabo Publishing Co., Ltd.), p. 143. Specifically, for example, as shown in the following formulae, a facial isomer is an isomer having a structure in which $R^b$ is always present on the extension of the bond between $R^a$ and Ir via O. Meanwhile, a meridional isomer is an isomer having a structure in which not only $R^b$ but also $R^a$ may be present on the extension of the bond between $R^a$ and Ir via O, and not only $R^a$ but also $R^b$ may be present on the extension of the bond between $R^b$ and Ir via O.

Geometric Isomers of an Iridium Raw Material Represented by General Formula (1)

[Chemical Formula 10]

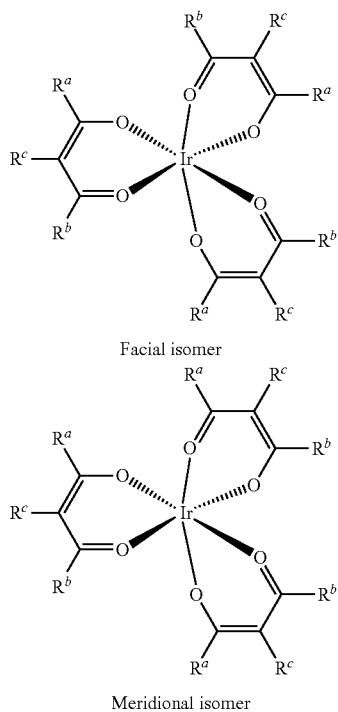

Facial isomer

Meridional isomer

When an iridium raw material of General Formula (1) is produced, it is often obtained as a mixture of facial and meridional isomers. These geometric isomers can be separated into a facial isomer and a meridional isomer by a method such as column chromatography or distillation according to the purpose. For example, in the iridium raw material (A-3) or (A-7) described above, the geometric isomers can be separated by silica gel chromatography.

As a raw material for a cyclometalated iridium complex, in terms of operability in the cyclometalated iridium complex production process, using a mixture of facial and meridional isomers is also preferable. As a mixture, in particular, either geometric isomer is preferably contained in a proportion of 0.01 mol % or more, preferably 0.1 mol % or more, more preferably 1 mol % or more, and particularly preferably 10 mol % or more. Geometric isomers can be identified by analysis with various devices, such as $^1$H-NMR. The facial isomer content and the meridional isomer content can each be quantified using $^1$H-NMR, gas chromatography, high-speed liquid chromatography, or the like.

As described above, a cyclometalated iridium complex can be produced by a method including a step of allowing an organic iridium material coordinated with an asymmetric β-diketone (raw material) to react with an aromatic heterocyclic bidentate ligand capable of forming an iridium-carbon bond. By applying the raw material of the present invention, a cyclometalated iridium complex can be obtained in a single step in higher yield at a lower reaction temperature than using tris(2,4-pentanedionato)iridium(III).

Hereinafter, the method for producing a cyclometalated iridium complex will be described in detail.

The aromatic heterocyclic bidentate ligand to react with the organic iridium material (raw material) is an aromatic heterocyclic bidentate ligand capable of forming an iridium-carbon bond, preferably an aromatic heterocyclic bidentate ligand that forms one iridium-nitrogen bond and one iridium-carbon bond or an aromatic heterocyclic bidentate ligand that forms two iridium-carbon bonds, and more preferably an aromatic heterocyclic bidentate ligand that forms one iridium-nitrogen bond and one iridium-carbon bond.

More specifically, as the aromatic heterocyclic bidentate ligand, a 2-phenylpyridine derivative, a 2-phenylquinoline derivative, a 1-phenylisoquinoline derivative, a 3-phenylisoquinoline derivative, a 2-(2-benzothiophenyl)pyridine derivative, a 2-thienylpyridine derivative, a 1-phenylpyrazole derivative, a 1-phenyl-1H-indazole derivative, a 2-phenylbenzothiazole derivative, a 2-phenylthiazole derivative, a 2-phenylbenzoxazole derivative, a 2-phenyloxazole derivative, a 2-furanylpyridine derivative, a 2-(2-benzofuranyl)pyridine derivative, a 7,8-benzoquinoline derivative, a 7,8-benzoquinoxaline derivative, a dibenzo[f,h]quinoline derivative, a dibenzo[f,h]quinoxaline derivative, a benzo[h]-5,6-dihydroquinoline derivative, a 9-(2-pyridyl)carbazole derivative, a 1-(2-pyridyl)indole derivative, a 1-(1-naphthyl)isoquinoline derivative, a 1-(2-naphthyl)isoquinoline derivative, a 2-(2-naphthyl)quinoline derivative, a 2-(1-naphthyl)quinoline derivative, a 3-(1-naphthyl)isoquinoline derivative, a 3-(2-naphthyl)isoquinoline derivative, a 2-(1-naphthyl)pyridine derivative, a 2-(2-naphthyl)pyridine derivative, a 6-phenylphenanthridine derivative, a 6-(1-naphthyl)phenanthridine derivative, a 6-(2-naphthyl)phenanthridine derivative, a benzo[c]acridine derivative, a benzo[c]phenazine derivative, a dibenzo[a,c]acridine derivative, a dibenzo[a,c]phenazine derivative, a 2-phenylquinoxaline derivative, a 2,3-diphenylquinoxaline derivative, a 2-benzylpyridine derivative, a 2-phenylbenzimidazole derivative, a 3-phenylpyrazole derivative, a 4-phenylimidazole derivative, a 1-phenylimidazole derivative, a 4-phenyltriazole derivative, a 5-phenyltetrazole derivative, a 2-alkenylpyridine derivative, a 5-phenyl-1,2,4-triazole derivative, an imidazo[1,2-f]phenanthridine derivative, a 1-phenylbenzimidazolium salt derivative, and a 1-phenylimidazolium salt derivative are preferable.

Among them, as the aromatic heterocyclic bidentate ligand, a 2-phenylpyridine derivative, a 2-phenylquinoline derivative, a 1-phenylisoquinoline derivative, a 3-phenylisoquinoline derivative, a 1-phenylpyrazole derivative, a 7,8-benzoquinoline derivative, a 7,8-benzoquinoxaline derivative, a dibenzo[f,h]quinoline derivative, a dibenzo[f,h]quinoxaline derivative, a benzo[h]-5,6-dihydroquinoline derivative, a 6-phenylphenanthridine derivative, a 2-phenylquinoxaline derivative, a 2,3-diphenylquinoxaline derivative, a 2-phenylbenzimidazole derivative, a 3-phenylpyrazole derivative, a 4-phenylimidazole derivative, a 1-phenylimidazole derivative, a 4-phenyltriazole derivative, a 5-phenyltetrazole derivative, a 5-phenyl-1,2,4-triazole derivative, a 1,2-imidazo[f]phenanthridine derivative, a 1-phenylbenzimidazolium salt derivative, and a 1-phenylimidazolium salt derivative are more preferable. In addition, a 2-phenylpyridine derivative, a 1-phenylisoquinoline derivative, a 1-phenylimidazole derivative, and a 1,2-imidazo[f]phenanthridine derivative are particularly preferable, and a 2-phenylpyridine derivative, a 1-phenylisoquinoline derivative, and a 1-phenylimidazole derivative are particularly preferable.

As the specific structure of the aromatic heterocyclic bidentate ligand used in the present invention, for example, the following structure examples 1 to 3 can be mentioned. Among them, those having structures represented by General Formulae (3) to (7) are particularly preferable. In the structure examples 1 to 3 and General Formulae (3) to (7), * indicates a site of bonding to iridium.

Structure Example 1 of the Aromatic Heterocyclic Bidentate Ligand

[Chemical Formula 11]

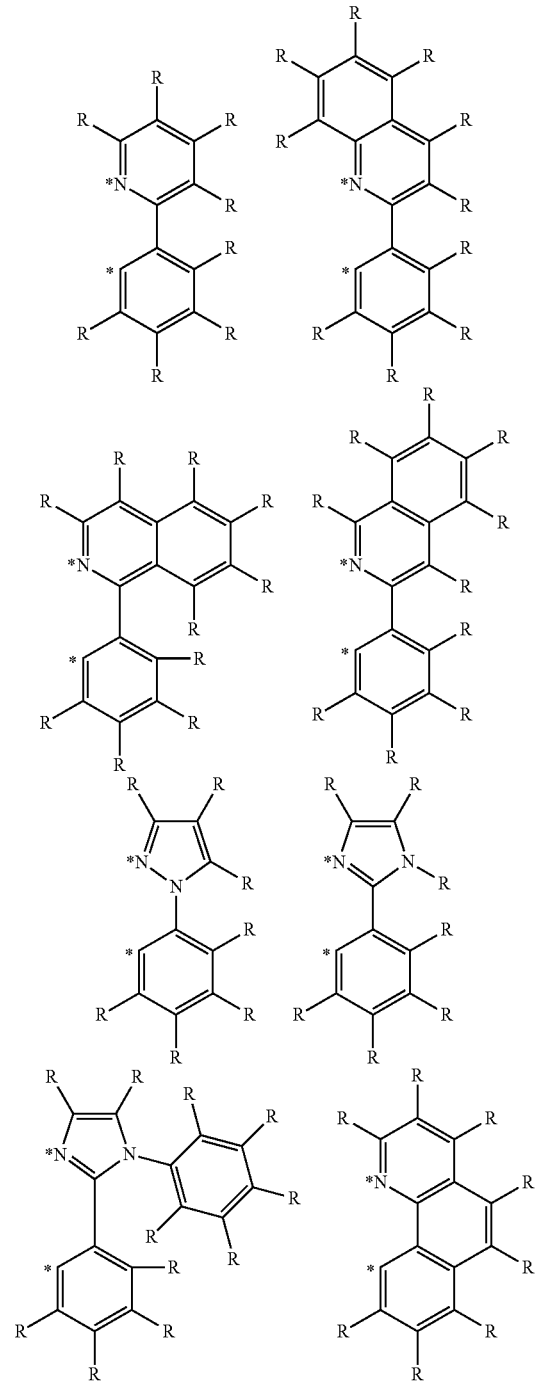

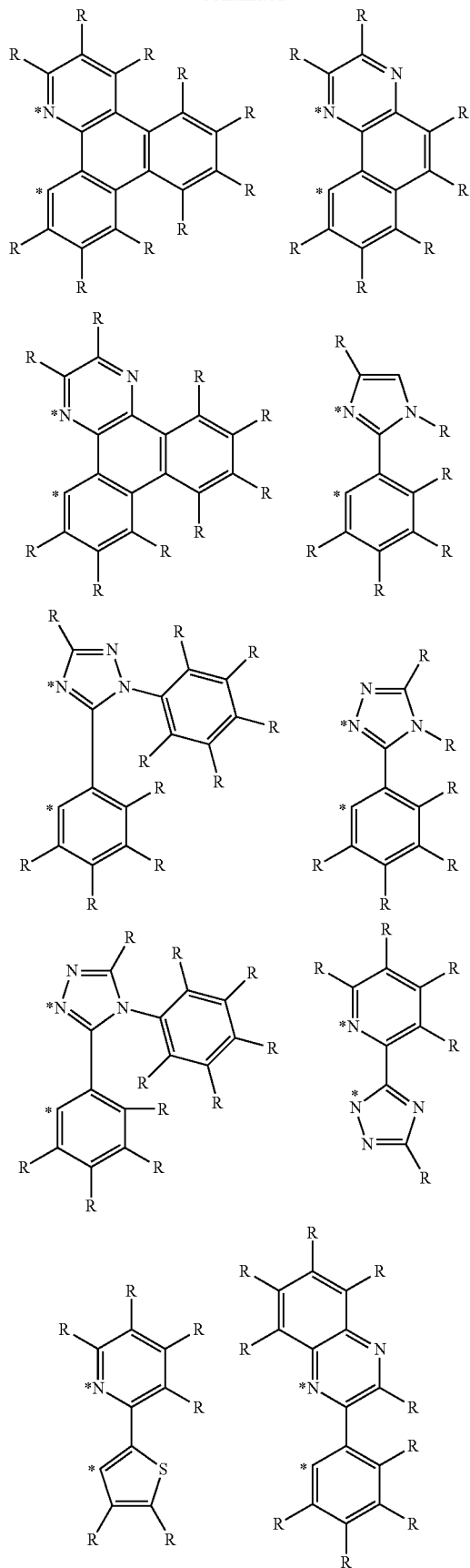

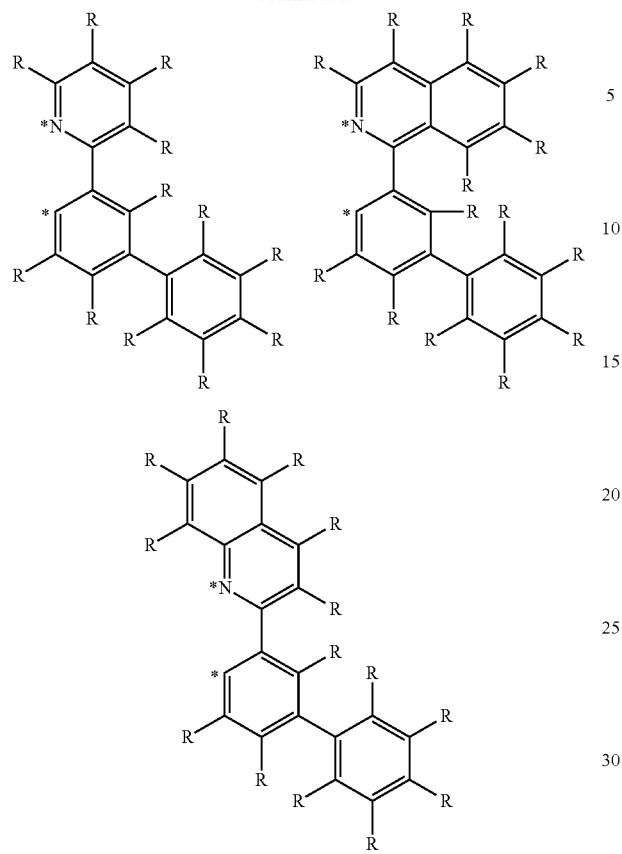
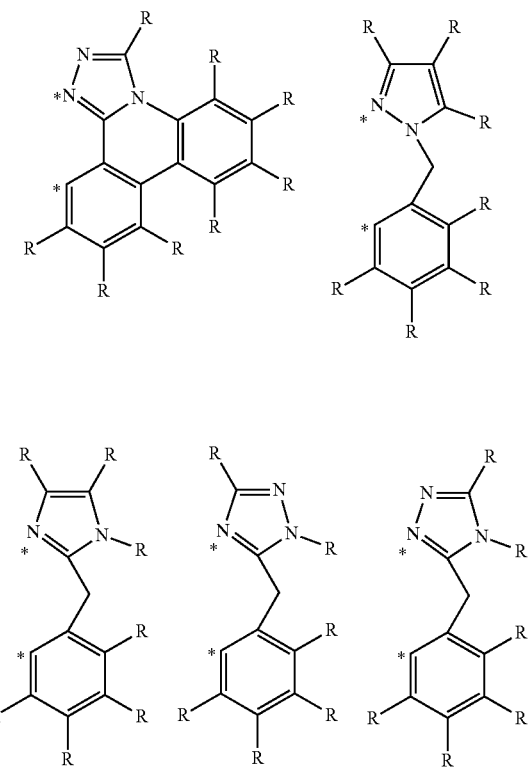
Structure Example 2 of the Aromatic Heterocyclic Bidentate Ligand
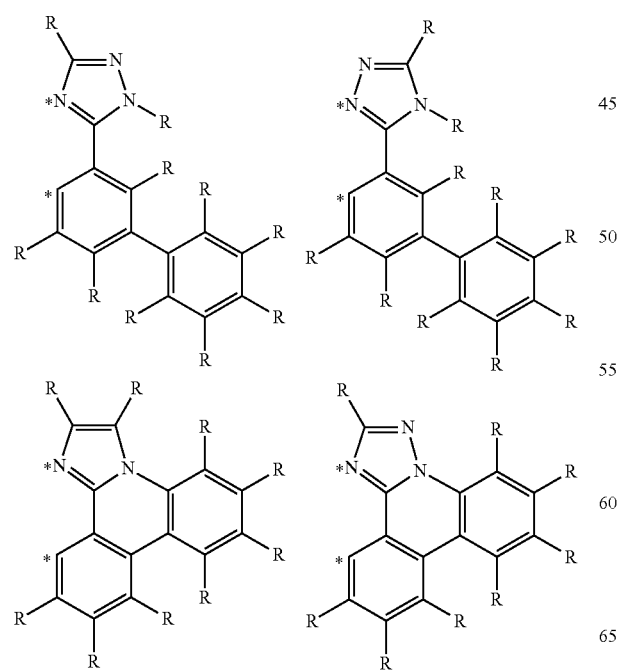
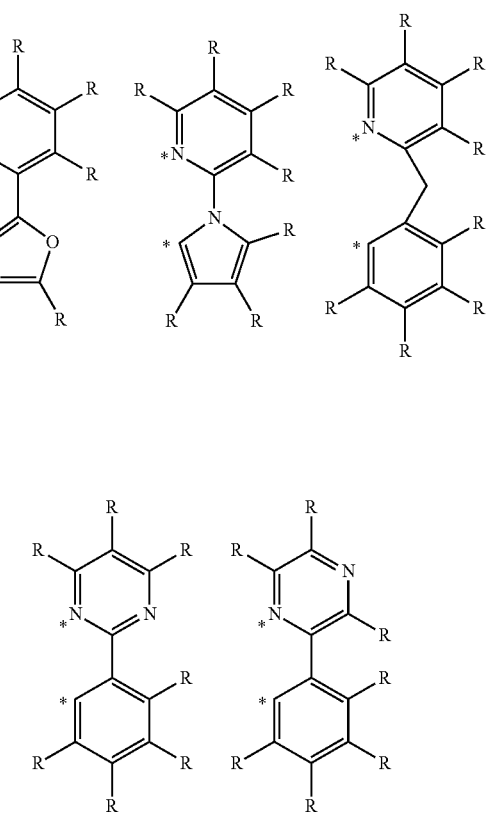

Structure Example 3 of the Aromatic Heterocyclic Bidentate Ligand
[Chemical Formula 13]
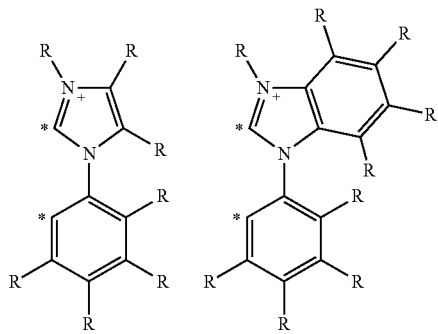
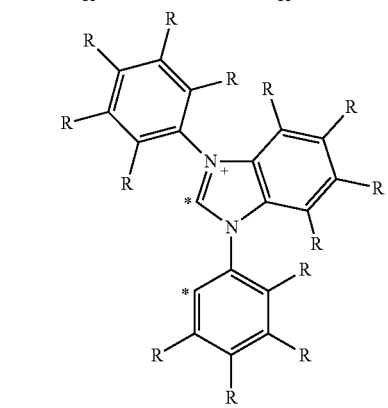
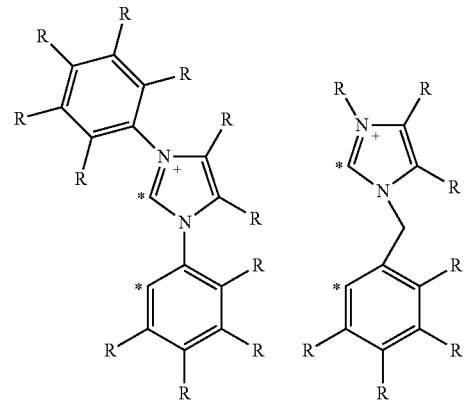
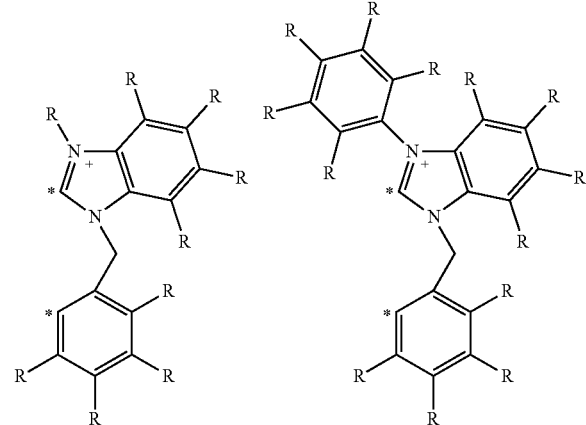
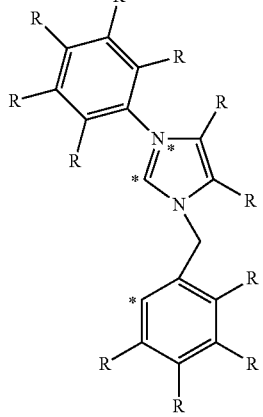
[Chemical Formula 14]
General Formula (3)
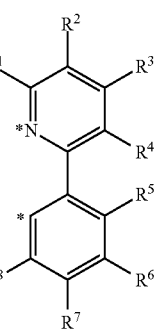
[Chemical Formula 15]
General Formula (4)
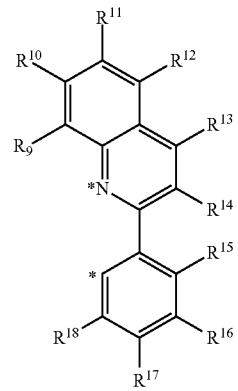
[Chemical Formula 16]
General Formula (5)
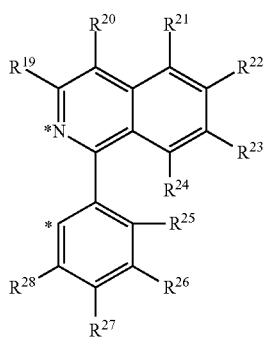

-continued

[Chemical Formula 17]

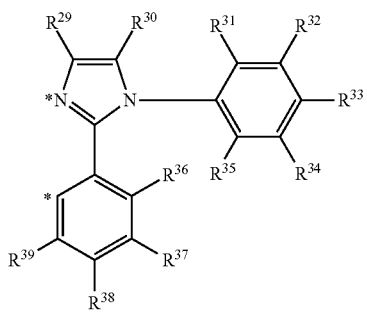

General Formula (6)

[Chemical Formula 18]

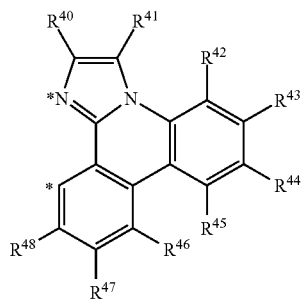

General Formula (7)

In the structure examples 1 to 3 and General Formulae (3) to (7), R and $R^1$ to $R^{48}$ are each a hydrogen atom or the following substituent. Examples of substituents include alkyl groups (preferably $C_{1-30}$, more preferably $C_{1-20}$, and particularly preferably $C_{1-10}$, such as methyl, ethyl, isopropyl, tert-butyl, n-octyl, n-decyl, n-hexadecyl, cyclopropyl, cyclopentyl, and cyclohexyl), alkenyl groups (preferably $C_{2-30}$, more preferably $C_{2-20}$, and particularly preferably $C_{2-10}$, such as vinyl, allyl, 2-butenyl, and 3-pentenyl), alkynyl groups (preferably $C_{2-30}$, more preferably $C_{2-20}$, and particularly preferably $C_{2-10}$, such as propargyl and 3-pentynyl), aryl groups (preferably $C_{6-30}$, more preferably $C_{6-20}$, and particularly preferably $C_{6-12}$, such as phenyl, p-methylphenyl, naphthyl, and anthranil), amino groups (preferably $C_{0-30}$, more preferably $C_{0-20}$, and particularly preferably $C_{0-10}$, such as amino, methylamino, dimethylamino, diethylamino, dibenzylamino, diphenylamino, and ditolylamino), alkoxy groups (preferably $C_{1-30}$, more preferably $C_{1-20}$, and particularly preferably $C_{1-10}$, such as methoxy, ethoxy, butoxy, and 2-ethylhexyloxy), aryloxy groups (preferably $C_{6-30}$, more preferably $C_{6-20}$, and particularly preferably $C_{6-12}$, such as phenyloxy, 1-naphthyloxy, and 2-naphthyloxy), heterocyclic oxy groups (preferably $C_{1-30}$, more preferably $C_{1-20}$, and particularly preferably $C_{1-12}$, such as pyridyloxy, pyrazyloxy, pyrimidyloxy, and quinolyloxy), acyl groups (preferably $C_{1-30}$, more preferably $C_{1-20}$, and particularly preferably $C_{1-12}$, such as acetyl, benzoyl, formyl, and pivaloyl), alkoxycarbonyl groups (preferably $C_{2-30}$, more preferably $C_{2-20}$, and particularly preferably $C_{2-12}$, such as methoxycarbonyl and ethoxycarbonyl), aryloxycarbonyl groups (preferably $C_{7-30}$, more preferably $C_{7-20}$, and particularly preferably $C_{7-12}$, such as phenyloxycarbonyl), acyloxy groups (preferably $C_{2-30}$, more preferably $C_{2-20}$, and particularly preferably $C_{2-10}$, such as acetoxy and benzoyloxy), acylamino groups (preferably $C_{2-30}$, more preferably $C_{2-20}$, and particularly preferably $C_{2-10}$, such as acetylamino and benzoylamino), alkoxycarbonylamino groups (preferably $C_{2-30}$, more preferably $C_{2-20}$, and particularly preferably $C_{2-12}$, such as methoxycarbonylamino), aryloxycarbonylamino groups (preferably $C_{7-30}$, more preferably $C_{7-20}$, and particularly preferably $C_{7-12}$, such as phenyloxycarbonylamino), sulfonylamino groups (preferably $C_{1-30}$, more preferably $C_{1-20}$, and particularly preferably $C_{1-12}$, such as methanesulfonylamino and benzenesulfonylamino), sulfamoyl groups (preferably $C_{0-30}$, more preferably $C_{0-20}$, and particularly preferably $C_{0-12}$, such as sulfamoyl, methylsulfamoyl, dimethylsulfamoyl, and phenylsulfamoyl), carbamoyl groups (preferably $C_{1-30}$, more preferably $C_{1-20}$, and particularly preferably $C_{1-12}$, such as carbamoyl, methylcarbamoyl, diethylcarbamoyl, and phenylcarbamoyl), alkylthio groups (preferably $C_{1-30}$, more preferably $C_{1-20}$, and particularly preferably $C_{1-12}$, such as methylthio and ethylthio), arylthio groups (preferably $C_{6-30}$, more preferably $C_{6-20}$, and particularly preferably $C_{6-12}$, such as phenylthio), heterocyclic thio groups (preferably $C_{1-30}$, more preferably $C_{1-20}$, and particularly preferably $C_{1-12}$, such as pyridylthio, 2-benzimizolylthio, 2-benzoxazolylthio, and 2-benzothiazolylthio), sulfonyl groups (preferably $C_{1-30}$, more preferably $C_{1-20}$, and particularly preferably $C_{1-12}$, such as mesyl and tosyl), sulfinyl groups (preferably $C_{1-30}$, more preferably $C_{1-20}$, and particularly preferably $C_{1-12}$, such as methanesulfinyl and benzenesulfinyl), ureide groups (preferably $C_{1-30}$, more preferably $C_{1-20}$, and particularly preferably $C_{1-12}$, such as ureide, methylureide, and phenylureide), phosphoramide groups (preferably $C_{1-30}$, more preferably $C_{1-20}$, and particularly preferably $C_{1-12}$, such as diethylphosphoramide and phenylphosphoramide), a hydroxyl group, a mercapto group, halogen atoms (such as a fluorine atom, a chlorine atom, a bromine atom, and an iodine atom), a cyano group, a sulfo group, a carboxyl group, a nitro group, a trifluoromethyl group, a hydroxamic acid group, a sulfino group, a hydrazino group, an imino group, heterocyclic groups (preferably $C_{1-30}$, more preferably $C_{1-12}$, examples of heteroatoms including a nitrogen atom, an oxygen atom, and a sulfur atom; specifically, imidazolyl, pyridyl, quinolyl, furyl, thienyl, piperidyl, morpholino, benzoxazolyl, benzimidazolyl, benzothiazolyl, a carbazolyl group, an azepinyl group, etc.), silyl groups (preferably $C_{3-40}$, more preferably $C_{3-30}$, and particularly preferably $C_{3-24}$, such as trimethylsilyl and triphenylsilyl), and silyloxy groups (preferably $C_{3-40}$, more preferably $C_{3-30}$, and particularly preferably $C_{3-24}$, such as trimethylsilyloxy and triphenylsilyloxy). Particularly preferred substituents are a cyano group, a trifluoromethyl group, halogen atoms, alkyl groups, aryl groups, amino groups, and heterocyclic groups.

Then, the reaction to synthesize a cyclometalated iridium complex is carried out by allowing the iridium raw material of the present invention represented by General Formula (1) to react with the above aromatic heterocyclic bidentate ligand.

The above reaction may be carried out in air or an inert gas (nitrogen, argon, etc.) atmosphere, and is preferably performed in an inert gas atmosphere.

In the present invention, in order for the above reaction to proceed more smoothly, a solvent may be added to the reaction system of the synthesis reaction. When no solvent is added, the reaction temperature of the synthesis reaction is preferably 200° C. to 300° C., and the reaction time is preferably 10 hours to 20 hours.

Examples of solvents added to the reaction system include various kinds of organic solvents, such as saturated aliphatic hydrocarbons, halogenated aliphatic hydrocarbons, ketones, amides, esters, aromatic hydrocarbons, halogenated aromatic hydrocarbons, nitrogen-containing aromatic compounds, ethers, nitryls, alcohols, and ionic liquids. Specific examples include tridecane, ethylene glycol, glycerin, 2-methoxyethanol, 2-ethoxyethanol, N,N-dimethylformamide, N-methylpyrrolidone, imidazolium salt, dimethyl sulfoxide, 1,2-propanediol, 1,3-propanediol, and 1,3-butanediol. In addition, using a mixed solvent containing two or more kinds of the above solvents is also preferable.

As the above solvents, those having a boiling point of 160° C. to 300° C. at ambient pressure are preferable, more preferably 170° C. to 300° C., and particularly preferably 180° C. to 300° C.

When a solvent is used in the synthesis of a cyclometalated iridium complex, the concentration of the iridium raw material of General Formula (1) in the reaction system is not limited, but is preferably 0.001 mol/L to 10.0 mol/L, more preferably 0.001 mol/L to 1.0 mol/L, particularly preferably 0.01 mol/L to 1.0 mol/L, and most preferably 0.05 mol/L to 0.5 mol/L.

The organic iridium raw material of General Formula (1) has an asymmetric structure including an asymmetric β-diketone, thus has a low melting point, and is likely to be in a liquid state at room temperature or turn into a liquid state upon heating. Therefore, this raw material is also particularly suitable for synthesis in the absence of a solvent.

In the cyclometalated iridium complex synthesis reaction described above, an acidic substance or a basic substance may be suitably added in order to promote the reaction. An acidic substance promotes the release of the β-diketone ligands, while a basic substance promotes the cyclometalation reaction of the aromatic heterocyclic bidentate ligand. However, the addition of an acidic substance or a basic substance may cause the decomposition of the iridium raw material, aromatic heterocyclic bidentate ligand, or cyclometalated iridium complex, which tends to reduce the yield or purity of the cyclometalated iridium complex. Accordingly, it is desirable that no acidic substance or basic substance is added. Specifically, When the aromatic heterocyclic bidentate ligand of General Formula (6) or General Formula (7) is used, addition of acidic substance to the reaction system significantly decreases the yield of the cyclometalated iridium complex, and the complex is hardly obtained in many cases.

When an acidic substance is added as above, one that acts as a proton source in the reaction system or one that is capable of receiving an electron pair, such as a Lewis acid or a solid acid can be applied. Particularly, Bronsted acids including organic acids such as acetic acid, oxalic acid, valeric acid, butanoic acid, and tartaric acid, inorganic acids such as hydrochloric acid, sulfuric acid, and phosphoric acid, and the like are preferable. They may be used alone or as a mixture of two or more kinds. Additionally, these acidic substances preferably have a boiling point of 150° C. or more, because when the boiling point of the acidic substance is lower than the reaction temperature, the acidic substance refluxes, whereby the temperature in the reaction system is unlikely to rise to the temperature sufficient for the reaction to proceed.

When an acidic substance is added, the molar ratio between the acidic substance and the iridium raw material should be such that the amount of acidic substance is 0.5 mol or more per mol of the iridium raw material, preferably 0.5:1 to 20:1 (acidic substance:iridium raw material), and more preferably 3:1 to 20:1. When the amount of acidic substance is less than 0.5 mol per mol of the iridium raw material, the reaction-promoting effect cannot be sufficiently obtained, and the reaction cannot be completed within a short period of time; therefore, this is undesirable. When the amount of acidic substance is more than 0.5 mol per mol of the iridium raw material, although there is no particular upper limit, the addition of a needlessly large amount of acidic substance is economically inefficient.

When a basic substance is added, it may be an alkali-metal-containing inorganic base, an organic amine such as an aliphatic amine or an aromatic amine, an alkali metal alkoxide, or the like. They may be used alone or as a mixture of two or more kinds. For example, sodium hydrogen carbonate, potassium hydrogen carbonate, sodium carbonate, potassium carbonate, sodium hydroxide, potassium hydroxide, trimethylamine, triethylamine, tripropylamine, tributylamine, triethanolamine, triisopropylamine, triisobutylamine, proton sponge, diazabicycloundecen, pyridine, 2-phenylpyridine, sodium methoxide, sodium-t-butoxide, and potassium-t-butoxide are included. Sodium hydrogen carbonate, potassium hydrogen carbonate, sodium carbonate, potassium carbonate, triethanolamine, and the like are preferable, and sodium carbonate and potassium carbonate are particularly preferable.

When a basic substance is added, the molar ratio between the basic substance and the iridium raw material is preferably such that the amount of basic substance is 0.001 mol or more per mol of the iridium raw material, more preferably 0.01:1 to 5:1 (basic substance:iridium raw material), and particularly preferably 0.01:1 to 3:1. Although the amount of basic substance used is not limited, when the amount is needlessly large, this results in the decomposition of the iridium raw material of General Formula (1) and thus is undesirable.

In the synthesis of a cyclometalated iridium complex, the reaction temperature is preferably 100° C. to 300° C., more preferably 150° C. to 300° C., and particularly preferably 180° C. to 300° C.

In the synthesis of a cyclometalated iridium complex, the reaction time is preferably 1 to 100 hours, more preferably 3 to 80 hours, and particularly preferably 5 to 50 hours.

In the synthesis of a cyclometalated iridium complex, the heating method is not particularly limited. Specifically, external heating using an oil bath, a sand bath, a mantle heater, a block heater, or a heat-circulation jacket, as well as heating by irradiation with microwaves can be utilized, for example.

The synthesis of a cyclometalated iridium complex is usually performed at ambient pressure, but may also be performed under increased pressure or reduced pressure as necessary.

In the synthesis of a cyclometalated iridium complex, the amount of aromatic heterocyclic bidentate ligand used is not particularly limited, but is preferably 3 to 100 times, more preferably 3 to 50 times, particularly preferably 3 to 30 times, and most preferably 3 to 10 times, the molar amount of the iridium raw material.

In the production method of the present invention, the asymmetric β-diketone by-produced in the cyclometalated iridium complex is also preferably distilled from the reaction system during the synthesis. The method for distilling the β-diketone is not particularly limited, but the methods described in JP 2004-337802 A, WO 2006/014599, etc., may be used, for example.

The cyclometalated iridium complex obtained by the synthesis method described above is treated by a general post-treatment method and then, after purification as necessary or without purification, can be used as a high-purity product. As the method for post-treatment, for example, extraction, cooling, crystallization by adding water or an organic solvent, distillation of the solvent from the reaction mixture, and like operations may be performed alone or in combination. As the method for purification, recrystallization, distillation, sublimation, column chromatography, and the like may be performed alone or in combination.

The cyclometalated iridium complex to be produced by the production method of the present invention is preferably a biscyclometalated iridium complex or a triscyclometalated iridium complex, more preferably a triscyclometalated iridium complex. Specific examples of such cyclometalated iridium complexes are described in JP 2007-224025 A, JP 2006-290891 A, JP 2006-213723 A, JP 2006-111623 A, JP 2006-104201 A, JP 2006-063080 A, JP 2009-541431 A, JP 2009-526071 A, JP 2008-505076 A, JP 2007-513159 A, JP 2007-513158 A, JP 2002-540572 A, JP 2009-544167 A, JP 2009-522228 A, JP 2008-514005 A, JP 2008-504342 A, JP 2007-504272 A, JP 2006-523231 A, JP 2005-516040 A, WO 2010/086089 A1, etc.

Then, as the reasons that the use of an iridium raw material of General Formula (1) improves the yield of the cyclometalated iridium complex, several factors are possible. Therefore, a single factor has not been specified, but the opinion of the present inventors is as follows.

First, it can be said that the β-diketone ligands forming the raw material of the present invention have a higher boiling point as compared with 2,4-pentanedione, which serves as ligands in tris(2,4-pentanedionato)iridium(III), and the β-diketone produced with the progress of the reaction is unlikely to reduce the temperature of the reaction solution.

Next, the raw material of the present invention has asymmetric β-diketone ligands, thus has reduced crystallinity and also a reduced melting point, and is likely to turn into a liquid state at room temperature or upon heating. This tendency is particularly prominent when two kinds of geometric isomers are contained. It is considered that when the raw material turns into a liquid state, the affinity with the aromatic heterocyclic bidentate ligand is improved, resulting in the excellent reactivity.

Further, the raw material of the present invention turns into a liquid state upon heating during the cyclometalated iridium complex synthesis reaction, whereby sublimation is suppressed. Thus, it is considered that the problem of tris(2,4-pentanedionato)iridium(III) (the problem that the raw material is removed out of the reaction system due to sublimation) has been solved.

In addition, it is considered that in the raw material of the present invention, the β-diketone ligands are likely to be released at a lower temperature than tris(2,4-pentanedionato)iridium(III). This has been revealed as a result of evaluating the thermal stability of iridium raw materials using a TG-DTA simultaneous measuring instrument (see the below Examples).

It is considered that the several factors as described above are intricately combined, making it possible to improve the yield of the cyclometalated iridium complex by use of the iridium raw material of the present invention represented by General Formula (1).

In the cyclometalated iridium complex obtained using the raw material of the present invention, chlorine derived from the iridium raw material, which adversely affects the characteristics of a luminescent device, is not contained. When this complex is contained in a light-emitting layer or a plurality of organic compound layers including a light-emitting layer in a luminescent device, such a luminescent device can be provided with better light-emitting efficiency and durability than before.

Advantageous Effects of the Invention

As described above, in the present invention, a cyclometalated iridium complex can be obtained in better yield at a lower reaction temperature than using tris(2,4-pentanedionato)iridium (III).

EXAMPLES

Next, the present invention will be described in detail with reference to the Examples, but the present invention is not limited thereto. The structures of the compounds used in the Examples are as follows.

[Chemical Formula 19]

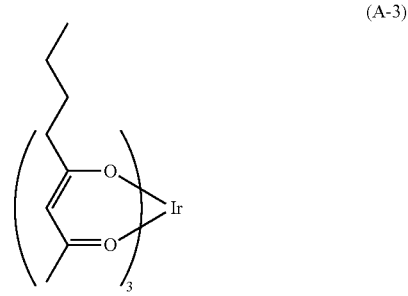

(A-3)

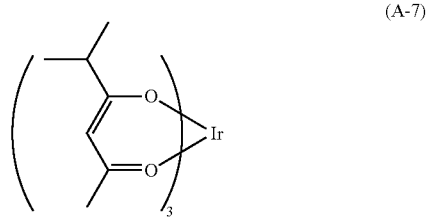

(A-7)

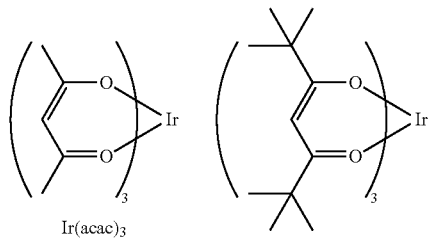

Ir(acac)$_3$

Ir(DPM)$_3$
Described in WO
2011/157339

Compound (A)

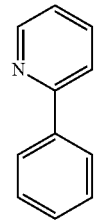

-continued

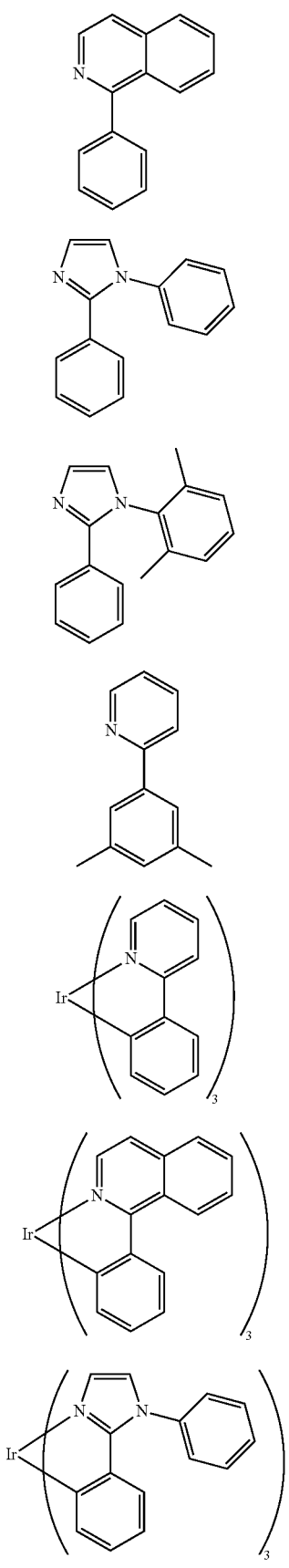

Compound (B)
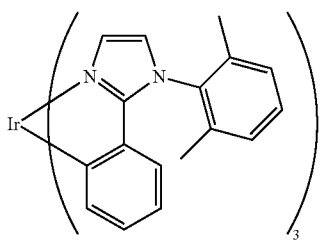

Compound (C)
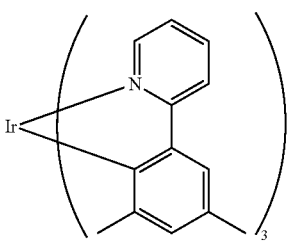

Compound (D)
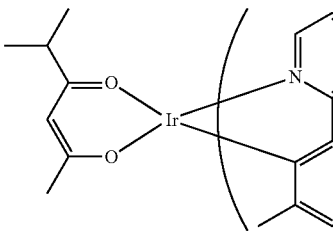

Compound (E)

-continued

Compound (4)

Compound (5)
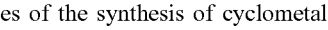

Compound (6)

(A-3), which is an iridium raw material in the present invention, was synthesized with reference to JP 2003-321416 A. As a result of analysis using $^1$H-NMR, gas chromatography, and high-speed liquid chromatography, the molar ratio between facial and meridional isomers was 1:3. The raw material was directly used in the following examples of the synthesis of cyclometalated iridium complexes.

(A-7), which is an iridium raw material in the present invention, was synthesized with reference to JP 2003-64019 A. As a result of analysis using $^1$H-NMR, gas chromatography, and high-speed liquid chromatography, the molar ratio between facial and meridional isomers was 1:3. The raw material was directly used in the following examples of the synthesis of cyclometalated iridium complexes.

Tris(2,4-pentanedionato)iridium(III) and tris(dipivaloylmethanato)iridium(III) [Ir(DPM)$_3$], which are known iridium raw materials, were synthesized with reference to JP 7-316176 A, JP 8-85873 A, etc. They were used in the following examples of the synthesis of cyclometalated iridium complexes (comparative examples).

<Example 1> Synthesis of Compound (1)

Compound (A-7) (344 mg), Compound (A) (558 mg), and ethylene glycol (30 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (1). The isolation yield of Compound (1) was 22%. Incidentally, the obtained Compound (1) was a facial isomer, and no meridional isomer was detected in $^1$H-NMR.

<Example 2> Synthesis of Compound (1)

Compound (A-7) (95 mg), Compound (A) (158 mg), and ethylene glycol (8.5 ml) were allowed to react by heating in an argon atmosphere at 140° C. (oil bath temperature) for 15 hours. The reaction mixture was cooled to room temperature, and then the precipitated solid was washed with methanol. The compound was identified using $^1$H-NMR and confirmed to be Compound (1). The isolation yield of Compound (1) was 9%. Incidentally, the obtained Compound (1) was a facial isomer, and no meridional isomer was detected in $^1$H-NMR.

<Example 3> Synthesis of Compound (1)

Compound (A-7) (344 mg), Compound (A) (558 mg), and 1,3-propanediol (5 ml) were allowed to react by heating in an argon atmosphere at 190° C. (oil bath temperature) for 15 hours. The reaction mixture was cooled to room temperature, and then the precipitated solid was washed with methanol. The compound was identified using $^1$H-NMR and confirmed to be Compound (1). The isolation yield of Compound (1) was 35%. Incidentally, the obtained Compound (1) was a facial isomer, and no meridional isomer was detected in $^1$H-NMR.

<Example 4> Synthesis of Compound (1)

Compound (A-3) (369 mg), Compound (A) (558 mg), and ethylene glycol (5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (1). The isolation yield of Compound (1) was 7%. Incidentally, the obtained Compound (1) was a facial isomer, and no meridional isomer was detected in $^1$H-NMR.

<Comparative Example 1> Synthesis of Compound (1)

Tris(2,4-pentanedionato)iridium(III) (98 mg), Compound (A) (186 mg), and ethylene glycol (5 ml) were allowed to react by heating in an argon atmosphere at 180° C. (oil bath temperature) for 15 hours. Compound (1) was not obtained at all.

<Comparative Example 2> Synthesis of Compound (1)

Tris(2,4-pentanedionato)iridium(III) (98 mg), Compound (A) (186 mg), and ethylene glycol (5 ml) were allowed to react by heating in an argon atmosphere at 140° C. (oil bath temperature) for 15 hours. Compound (1) was not obtained at all.

<Comparative Example 3> Synthesis of Compound (1)

Ir(DPM)$_3$ (71 mg), Compound (A) (93 mg), and ethylene glycol (5 ml) were allowed to react by heating in an argon atmosphere at 180° C. (oil bath temperature) for 15 hours. Compound (1) was not obtained at all.

<Example 5> Synthesis of Compound (1)

Compound (A-7) (344 mg), Compound (A) (558 mg), an 85% aqueous phosphoric acid solution (69 mg), and ethylene glycol (5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (1). The isolation yield of Compound (1) was 36%. Incidentally, the obtained Compound (1) was a facial isomer, and no meridional isomer was detected in $^1$H-NMR.

<Comparative Example 4> Synthesis of Compound (1)

Tris(2,4-pentanedionato)iridium(III) (98 mg), Compound (A) (186 mg), an 85% aqueous phosphoric acid solution (69 mg), and ethylene glycol (10 ml) were allowed to react in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (1). The isolation yield of Compound (1) was 12%. Incidentally, the obtained Compound (1) was a facial isomer, and no meridional isomer was detected in $^1$H-NMR.

<Example 6> Synthesis of Compound (1)

Compound (A-7) (344 mg), Compound (A) (558 mg), an 85% aqueous phosphoric acid solution (69 mg), and ethylene glycol (5 ml) were placed in a recovery flask, set to a microwave applicator equipped with a reflux condenser, and then irradiated with microwaves in an argon atmosphere for 30 minutes. The reaction mixture was cooled to room temperature, and then the precipitated solid was washed with methanol. The compound was identified using $^1$H-NMR and confirmed to be Compound (1). The isolation yield of Compound (1) was 31%. Incidentally, the obtained Compound (1) was a facial isomer, and no meridional isomer was detected in $^1$H-NMR.

<Example 7> Synthesis of Compound (1)

Compound (A-3) (369 mg), Compound (A) (558 mg), an 85% aqueous phosphoric acid solution (69 mg), and ethylene glycol (5 ml) were placed in a recovery flask, set to a microwave applicator equipped with a reflux condenser, and then irradiated with microwaves in an argon atmosphere for 30 minutes. The reaction mixture was cooled to room temperature, and then the precipitated solid was washed with methanol. The compound was identified using $^1$H-NMR and confirmed to be Compound (1). The isolation yield of Compound (1) was 17%. Incidentally, the obtained Compound (1) was a facial isomer, and no meridional isomer was detected in $^1$H-NMR.

<Comparative Example 5> Synthesis of Compound (1)

Tris(2,4-pentanedionato)iridium(III) (294 mg), Compound (A) (558 mg), an 85% aqueous phosphoric acid solution (69 mg), and ethylene glycol (5 ml) were placed in a recovery flask, set to a microwave applicator equipped with a reflux condenser, and then irradiated with microwaves in an argon atmosphere for 30 minutes. The reaction mixture was cooled to room temperature, and then the precipitated solid was washed with methanol. The compound was identified using $^1$H-NMR and confirmed to be Compound (1). The isolation yield of Compound (1) was 8%. Incidentally, the obtained Compound (1) was a facial isomer, and no meridional isomer was detected in $^1$H-NMR.

<Example 8> Synthesis of Compound (1)

Compound (A-7) (344 mg) and Compound (A) (558 mg), with no solvent added to the reaction system, were allowed to react by heating in an argon atmosphere at 250° C. (sand bath temperature) for 17 hours. The reaction mixture was cooled to room temperature, and then the precipitated solid was washed with methanol. The compound was identified using $^1$H-NMR and confirmed to be Compound (1). The isolation yield of Compound (1) was 80%. Incidentally, the obtained Compound (1) was a facial isomer, and no meridional isomer was detected in $^1$H-NMR.

<Example 9> Synthesis of Compound (1)

Compound (A-7) (344 mg) and Compound (A) (558 mg), with no solvent added the reaction system, were allowed to react in an argon atmosphere at 250° C. (sand bath temperature) for 7 hours. The reaction mixture was cooled to room temperature, and then the precipitated solid was washed with methanol. The compound was identified using $^1$H-NMR and confirmed to be Compound (1). The isolation yield of Compound (1) was 55%. Incidentally, the obtained Compound (1) was a facial isomer, and no meridional isomer was detected in $^1$H-NMR.

<Comparative Example 6> Synthesis of Compound (1)

Tris(2,4-pentanedionato)iridium(III) (294 mg) and Compound (A) (558 mg), with no solvent added to the reaction system, were allowed to react by heating in an argon atmosphere at 250° C. (sand bath temperature) for 17 hours. The reaction mixture was cooled to room temperature, and then the precipitated solid was washed with methanol. The compound was identified using $^1$H-NMR and confirmed to be Compound (1). The isolation yield of Compound (1) was 57%. Incidentally, the obtained Compound (1) was a facial isomer, and no meridional isomer was detected in $^1$H-NMR.

<Comparative Example 7> Synthesis of Compound (1)

Tris(2,4-pentanedionato)iridium(III) (294 mg) and Compound (A) (558 mg), with no solvent added to the reaction system, were allowed to react by heating in an argon atmosphere at 250° C. (sand bath temperature) for 7 hours. The reaction mixture was cooled to room temperature, and then the precipitated solid was washed with methanol. The compound was identified using $^1$H-NMR and confirmed to be Compound (1). The isolation yield of Compound (1) was 30%. Incidentally, the obtained Compound (1) was a facial isomer, and no meridional isomer was detected in $^1$H-NMR.

<Example 10> Synthesis of Compound (2)

Compound (A-7) (344 mg), Compound (B) (738 mg), and ethylene glycol (5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (2). The isolation yield of Compound (2) was 25%. Incidentally, the obtained Compound (2) was a facial isomer, and no meridional isomer was detected in $^1$H-NMR.

<Comparative Example 8> Synthesis of Compound (2)

Tris(2,4-pentanedionato)iridium(III) (294 mg), compound (B) (738 mg), and ethylene glycol (5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (2). The isolation yield of Compound (2) was 8%. Incidentally, the obtained Compound (2) was a facial isomer, and no meridional isomer was detected in $^1$H-NMR.

<Example 11> Synthesis of Compound (3)

Compound (A-7) (172 mg), Compound (C) (396 mg), and ethylene glycol (2.5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (3). The isolation yield of Compound (3) was 18%. Incidentally, the obtained Compound (3) was a facial isomer, and no meridional isomer was detected in $^1$H-NMR.

<Comparative Example 9> Synthesis of Compound (3)

Tris(2,4-pentanedionato)iridium(III) (147 mg), Compound (C) (396 mg), and ethylene glycol (2.5 ml) were allowed to react by heating in an argon atmosphere at 180° C. (oil bath temperature) for 15 hours. Compound (3) was not obtained at all.

<Comparative Example 10> Synthesis of Compound (3)

Ir(DPM)$_3$ (71 mg), Compound (C) (132 mg), and ethylene glycol (5 ml) were allowed to react by heating in an argon atmosphere at 180° C. (oil bath temperature) for 15 hours. Compound (3) was not obtained at all.

<Example 12> Synthesis of Compound (3)

Compound (A-7) (172 mg), Compound (C) (396 mg), and ethylene glycol (2.5 ml) were allowed to react by heating in an argon atmosphere at 210° C. (oil bath temperature) for 15 hours. The reaction mixture was cooled to room temperature, and then the precipitated solid was washed with methanol. The compound was identified using $^1$H-NMR and confirmed to be Compound (3). The isolation yield of Compound (3) was 22%. Incidentally, the obtained Compound (3) was a facial isomer, and no meridional isomer was detected in $^1$H-NMR.

<Comparative Example 11> Synthesis of Compound (3)

Tris(2,4-pentanedionato)iridium(III) (147 mg), compound (C) (396 mg), and ethylene glycol (2.5 ml) were allowed to react by heating in an argon atmosphere at 210°

C. (oil bath temperature) for 15 hours. The reaction mixture was cooled to room temperature, and then the precipitated solid was washed with methanol. The compound was identified using $^1$H-NMR and confirmed to be Compound (3). The isolation yield of Compound (3) was 2%. Incidentally, the obtained Compound (3) was a facial isomer, and no meridional isomer was detected in $^1$H-NMR.

<Example 13> Synthesis of Compound (3)

Compound (A-7) (172 mg) and Compound (C) (396 mg), with no solvent added to the reaction system, were allowed to react by heating in an argon atmosphere at 250° C. (sand bath temperature) for 17 hours. The reaction mixture was cooled to room temperature, and then the precipitated solid was washed with methanol. The compound was identified using $^1$H-NMR and confirmed to be Compound (3). The isolation yield of Compound (3) was 63%. Incidentally, the obtained Compound (3) was a facial isomer, and no meridional isomer was detected in $^1$H-NMR.

<Comparative Example 12> Synthesis of Compound (3)

Tris(2,4-pentanedionato)iridium(III) (147 mg) and Compound (C) (396 mg), with no solvent added to the reaction system, were allowed to react by heating in an argon atmosphere at 250° C. (sand bath temperature) for 17 hours. The reaction mixture was cooled to room temperature, and then the precipitated solid was washed with methanol. The compound was identified using $^1$H-NMR and confirmed to be Compound (3). The isolation yield of Compound (3) was 16%. Incidentally, the obtained Compound (3) was a facial isomer, and no meridional isomer was detected in $^1$H-NMR.

<Example 14> Synthesis of Compound (3)

Compound (A-7) (172 mg), Compound (C) (396 mg), and tridecane (2.5 ml) were allowed to react by heating in an argon atmosphere at 250° C. (sand bath temperature) for 17 hours. The reaction mixture was cooled to room temperature, and then the precipitated solid was washed with methanol. The compound was identified using $^1$H-NMR and confirmed to be Compound (3). The isolation yield of Compound (3) was 27%. Incidentally, the obtained Compound (3) was a facial isomer, and no meridional isomer was detected in $^1$H-NMR.

<Comparative Example 13> Synthesis of Compound (3)

Tris(2,4-pentanedionato)iridium(III) (147 mg), Compound (C) (396 mg), and tridecane (2.5 ml) were allowed to react by heating in an argon atmosphere at 250° C. (sand bath temperature) for 17 hours. The reaction mixture was cooled to room temperature, and then the precipitated solid was washed with methanol. The compound was identified using $^1$H-NMR and confirmed to be Compound (3). The isolation yield of Compound (3) was 3%. Incidentally, the obtained Compound (3) was a facial isomer, and no meridional isomer was detected in $^1$H-NMR.

<Example 15> Synthesis of Compound (4)

Compound (A-7) (115 mg), Compound (D) (298 mg), and ethylene glycol (2.5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (4). The isolation yield of Compound (4) was 15%. Incidentally, the obtained Compound (4) was a facial isomer, and no meridional isomer was detected in $^1$H-NMR.

<Comparative Example 14> Synthesis of Compound (4)

Tris(2,4-pentanedionato)iridium(III) (98 mg), Compound (D) (298 mg), and ethylene glycol (2.5 ml) were allowed to react by heating in an argon atmosphere at 180° C. (oil bath temperature) for 15 hours. The reaction mixture was cooled to room temperature, and then the precipitated solid was washed with methanol. The compound was identified using $^1$H-NMR and confirmed to be Compound (4). The isolation yield of Compound (4) was 0.5%. Incidentally, the obtained Compound (4) was a facial isomer, and no meridional isomer was detected in $^1$H-NMR.

<Example 16> Synthesis of Compound (4)

Compound (A-7) (115 mg), Compound (D) (298 mg), and ethylene glycol (2.5 ml) were allowed to react by heating in an argon atmosphere at 210° C. (oil bath temperature) for 15 hours. The reaction mixture was cooled to room temperature, and then the precipitated solid was washed with methanol. The compound was identified using $^1$H-NMR and confirmed to be Compound (4). The isolation yield of Compound (4) was 30%. Incidentally, the obtained Compound (4) was a facial isomer, and no meridional isomer was detected in $^1$H-NMR.

<Comparative Example 15> Synthesis of Compound (4)

Tris(2,4-pentanedionato)iridium(III) (98 mg), Compound (D) (298 mg), and ethylene glycol (2.5 ml) were allowed to react by heating in an argon atmosphere at 210° C. (oil bath temperature) for 15 hours. The reaction mixture was cooled to room temperature, and then the precipitated solid was washed with methanol. The compound was identified using $^1$H-NMR and confirmed to be Compound (4). The isolation yield of Compound (4) was 10%. Incidentally, the obtained Compound (4) was a facial isomer, and no meridional isomer was detected in $^1$H-NMR.

<Example 17> Synthesis of Compound (5) and Compound (6)

Compound (A-7) (344 mg) and Compound (E) (659 mg), with no solvent added to the reaction system, were allowed to react by heating in an argon atmosphere at 270° C. (sand bath temperature) for 15 hours. The reaction mixture was cooled to room temperature, and then dichloromethane (5 ml) was added, followed by filtration through a Celite layer to remove the precipitate. The obtained orange filtrate was concentrated, and the precipitated solid was purified by silica gel chromatography (eluant:dichloromethane-hexane mixed solvent). The compounds were identified using $^1$H-NMR and confirmed to be Compound (5) and Compound (6). The isolation yield of Compound (5) was 27%. The isolation yield of Compound (6) was 60%. Incidentally, the obtained Compound (5) was a facial isomer, and no meridional isomer was detected in $^1$H-NMR.

<Comparative Example 16> Synthesis of Compound (5) and Compound (6)

Tris(2,4-pentanedionato)iridium(III) (294 mg) and Compound (E) (659 mg), with no solvent added to the reaction system, were allowed to react by heating in an argon atmosphere at 270° C. (sand bath temperature) for 15 hours. The reaction mixture was cooled to room temperature, and then dichloromethane (5 ml) was added, followed by filtration through a Celite layer to remove the precipitate. The obtained orange filtrate was concentrated, and the precipitated solid was purified by silica gel chromatography (eluant:dichloromethane-hexane mixed solvent). The compounds were identified using $^1$H-NMR and confirmed to be Compound (5) and Compound (6). The isolation yield of Compound (5) was 15%. The isolation yield of Compound (6) was 50%. Incidentally, the obtained Compound (5) was a facial isomer, and no meridional isomer was detected in $^1$H-NMR.

From the above examples and comparative examples, it turned out that when using the iridium raw material (A-3) or (A-7), a cyclometalated iridium complex can be synthesized in better yield as compared with the case of using tris(2,4-pentanedionato)iridium(III) or Ir(DPM)$_3$.

Next, in order to clarify the cause of improvement in the yield of the cyclometalated iridium complex, the thermal stability of (A-3), (A-7), and Ir(acac)$_3$ was analyzed using a TG-DTA simultaneous measuring instrument.

Specifically, the thermal stability of each organic iridium raw material was evaluated using a TG-DTA simultaneous measuring instrument. The temperature rise rate was set at 5° C./min, and the 5% weight loss temperature was measured in a nitrogen gas flow (200 ml/min) while raising the temperature at ambient pressure. The measurement results are shown in Table 1.

TABLE 1

| Organic iridium material | 5% Weight loss temperature | Remarks |
| --- | --- | --- |
| (A-3) | 213° C. | Example |
| (A-7) | 181° C. | Example |
| Ir (acac)$_3$ | 222° C. | Comparative example |

From Table 1, it turned out that the 5% weight loss temperatures of (A-3) and (A-7), which are examples, are 9° C. and 41° C. lower than that of Ir(acac)$_3$, which is a comparative example, respectively. This result suggests that the β-diketone ligands in (A-3) and (A-7) are released at lower temperatures than in Ir(acac)$_3$.

In the iridium raw material of the present invention represented by General Formula (1), β-diketone ligands are likely to be released at a lower temperature than in Ir(acac)$_3$. Thus, by using the iridium raw material of the present invention represented by General Formula (1), a cyclometalated iridium complex can synthesized in better yield under milder conditions.

INDUSTRIAL APPLICABILITY

The present invention makes it possible to produce a cyclometalated iridium complex in better yield than using tris(2,4-pentanedionato)iridium(III) as a raw material, and thus contributes to the provision of phosphorescent materials for organic EL, etc.

The invention claimed is:

1. A method for producing a cyclometalated iridium complex, comprising the step of reacting a raw material for a cyclometalated iridium complex including an organic iridium material and one or more aromatic heterocyclic bidentate ligand of Chemical Formula 2 in a solvent having a boiling point at normal pressure of 160° C. to 300° C., wherein the reaction temperature is 100° C. to 300° C., thereby producing a facial isomer of any one of triscyclometalated iridium complex of Chemical Formula 3, in which three aromatic heterocyclic bidentate ligands are coordinated to the iridium atom, wherein the raw material comprises an organic iridium material which is a tris(β-diketonato)iridium(III) represented by Chemical Formula 1, in which an asymmetric β-diketone is coordinated to iridium,

[Chemical Formula 1]

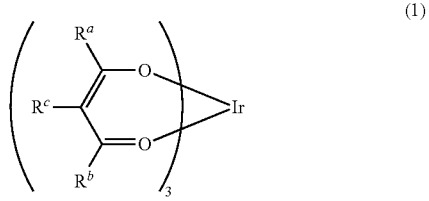

[Chemical Formula 2]

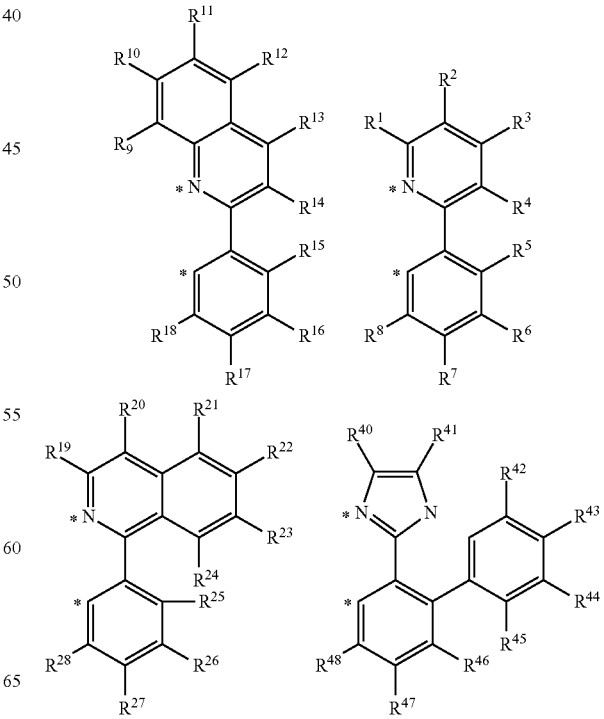

-continued

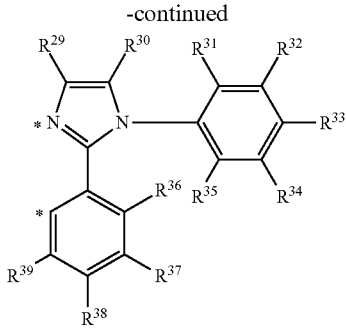

[Chemical Formula 3]

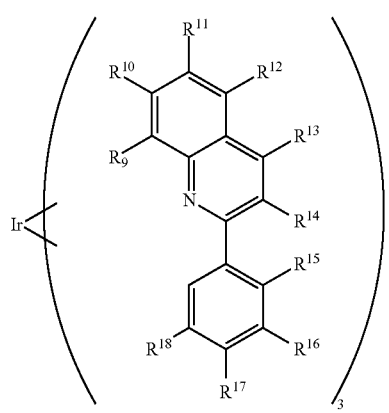

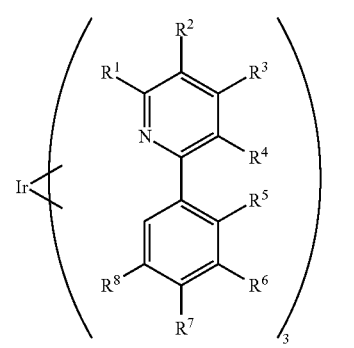

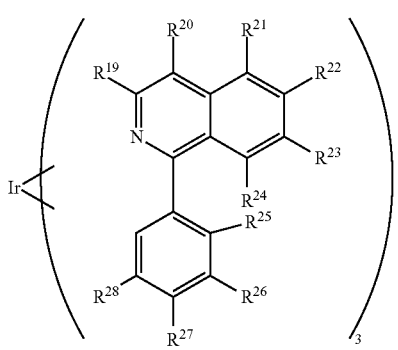

-continued

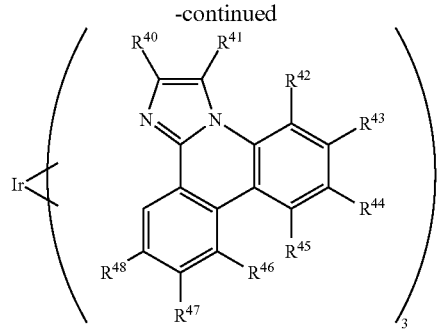

wherein in Chemical Formula 1, O represents an oxygen atom; $R^a$ and $R^b$ are each an alkyl group of $C_{1-5}$, and $R^a$ and $R^b$ are not the same; either $R^a$ or $R^b$ is a methyl group; and $R^c$ is a hydrogen atom, and wherein in Chemical Formula 2, $R^1$ to $R^{48}$ each represent a hydrogen atom, an alkyl group, an aryl group, or a halogen atom; and * indicates a site of bonding to iridium.

2. The method for producing a cyclometalated iridium complex according to claim 1, wherein the raw material and the aromatic heterocyclic bidentate ligand are reacted in the presence of acetic acid, oxalic acid, valeric acid, butyric acid, tartaric acid, hydrochloric acid, sulfuric acid, or phosphoric acid.

3. The method for producing a cyclometalated iridium complex according to claim 1, wherein $R^a$ and $R^b$ are each an aliphatic hydrocarbon group.

4. The method for producing a cyclometalated iridium complex according to claim 1, wherein $R^a$ and $R^b$ are each a linear or branched hydrocarbon group.

5. The method for producing a cyclometalated iridium complex according to claim 1, wherein the β-diketone is 5-methyl-2,4-hexanedione or 2,4-octanedione.

6. A method for producing a cyclometalated iridium complex, comprising the step of reacting a raw material for a cyclometalated iridium complex including an organic iridium material and one or more aromatic heterocyclic bidentate ligand of Chemical Formula 2 without solvent, wherein the reaction temperature is 200° C. to 300° C., thereby producing a facial isomer of any one of triscyclometalated iridium complex of Chemical Formula 3, in which three aromatic heterocyclic bidentate ligands are coordinated to the iridium atom, wherein the raw material comprises an organic iridium material which is a tris(β-diketonato)iridium(III) represented by Chemical Formula 1, in which an asymmetric β-diketone is coordinated to iridium,

[Chemical Formula 1]
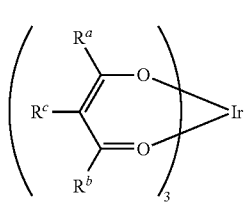
(1)
[Chemical Formula 2]
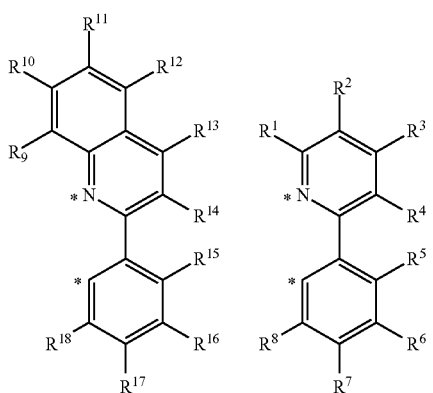
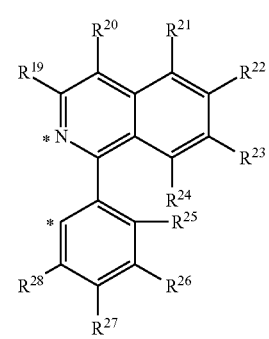
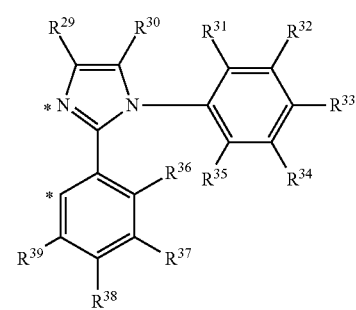
[Chemical Formula 3]
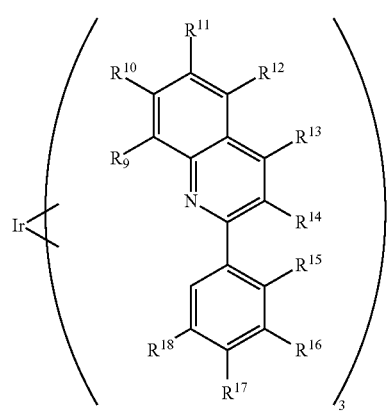
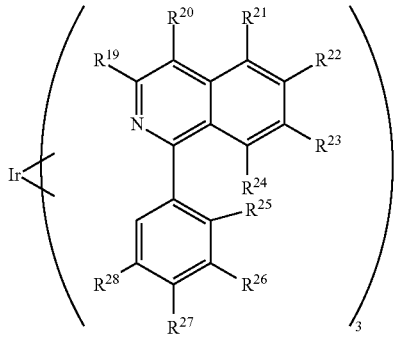
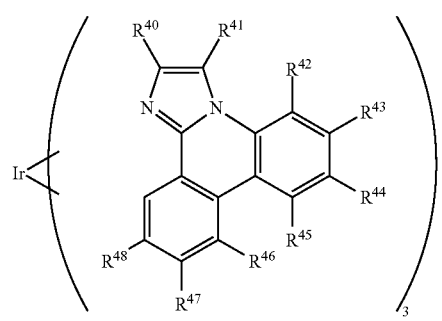

-continued
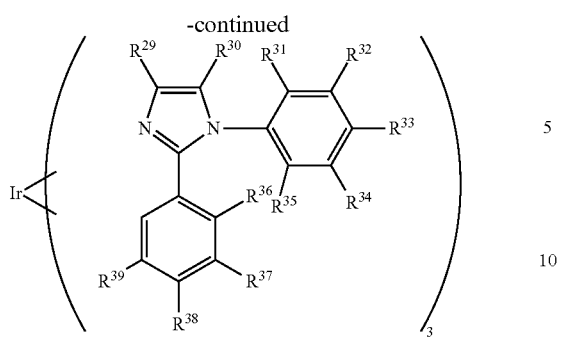
wherein in Chemical Formula 1, O represents an oxygen atom; $R_a$ and $R_b$ are each an alkyl group of $C_{1-5}$, and $R_a$ and $R_b$ are not the same; either $R_a$ or $R_b$ is a methyl group; and $R_c$ is a hydrogen atom, and wherein $R_1$ to $R_{48}$ each represent a hydrogen atom, an alkyl group, an aryl group, or a halogen atom; and * indicates a site of bonding to iridium.
* * * * *